US009897563B2

(12) United States Patent
Silveri

(10) Patent No.: US 9,897,563 B2
(45) Date of Patent: Feb. 20, 2018

(54) AMPEROMETRIC SENSOR SYSTEM

(71) Applicant: Michael A. Silveri, Incline Village, NV (US)

(72) Inventor: Michael A. Silveri, Incline Village, NV (US)

(\*) Notice: Subject to any disclaimer, the term of this patent is extended or adjusted under 35 U.S.C. 154(b) by 150 days.

(21) Appl. No.: 14/625,546

(22) Filed: Feb. 18, 2015

(65) Prior Publication Data

US 2015/0168342 A1 Jun. 18, 2015

Related U.S. Application Data

(62) Division of application No. 13/653,386, filed on Oct. 16, 2012, now Pat. No. 8,984,931, which is a division
(Continued)

(51) Int. Cl.
*G01N 27/08* (2006.01)
*G01N 27/06* (2006.01)
(Continued)

(52) U.S. Cl.
CPC ............. *G01N 27/08* (2013.01); *G01N 27/06* (2013.01); *F04D 1/04* (2013.01); *G01N 27/4168* (2013.01); *Y10T 29/49002* (2015.01)

(58) Field of Classification Search
CPC .................. G01N 27/06–27/10; Y10S 436/806
(Continued)

(56) References Cited

U.S. PATENT DOCUMENTS 3,438,872 A 4/1969 Johansson
3,474,330 A 10/1969 Dauphinee
(Continued)

FOREIGN PATENT DOCUMENTS

CN 1997890 A 7/2007
JP 2000009677 A 1/2000
(Continued)

OTHER PUBLICATIONS

"Wafer Testing Lab on a Chip," Innovation News 2001, article regarding Chemical Environmental Sensing Array (CENSAR), 1 page.
Censar 6-in-1 Water Quality Sensor, Censar Technologies, LLC, Burlington, Iowa, date unknown (in U.S. Appl. No. 12/167,171), 2 pages.
(Continued)

*Primary Examiner* — Peter Macchiarolo
*Assistant Examiner* — Nathaniel Kolb
(74) *Attorney, Agent, or Firm* — Patterson Intellectual Property Law, P.C.; Jerry Turner Sewell

(57) ABSTRACT

A sensor system that measures at least one parameter of water includes an electronics subsystem and includes a sensor housing electrically and mechanically coupled to the electronics subsystem. The sensor housing encloses a chamber that receives water via at least one inlet and that releases water via at least one outlet. At least one sensor has at least one electrode exposed to water in the chamber. A flow generator causes water to flow through the chamber. A plurality of objects within the chamber move in response to the water flow and abrasively clean the at least one electrode. Preferably, the sensor system includes a chlorine sensor having at least two electrodes. The electronics subsystem applies a first differential voltage between the two electrodes during a measurement interval and then applies a second differential voltage between the two electrodes during an interval following the measurement interval.

1 Claim, 16 Drawing Sheets

Related U.S. Application Data of application No. 13/372,260, filed on Feb. 13, 2012, now Pat. No. 8,887,556.

(60) Provisional application No. 61/597,832, filed on Feb. 12, 2012, provisional application No. 61/597,762, filed on Feb. 11, 2012, provisional application No. 61/548,953, filed on Oct. 19, 2011, provisional application No. 61/443,240, filed on Feb. 15, 2011.

(51) Int. Cl.
*G01N 27/416* (2006.01)
*F04D 1/04* (2006.01)

(58) Field of Classification Search
USPC .......... 422/82.01–82.04; 73/61.41; 205/775
See application file for complete search history.

(56) References Cited

U.S. PATENT DOCUMENTS

| | | | |
|---|---|---|---|
| 3,776,832 A | 12/1973 | Oswin et al. | |
| 3,913,384 A * | 10/1975 | Furuya | G01N 27/38 73/19.1 |
| 3,966,413 A * | 6/1976 | Marinenko | G01N 27/4045 204/406 |
| 3,975,271 A | 8/1976 | Saunier et al. | |
| 4,018,565 A * | 4/1977 | Fletcher, III | G01N 27/44 204/405 |
| 4,033,830 A | 7/1977 | Fletcher, III | |
| 4,224,154 A | 9/1980 | Steininger | |
| 4,233,031 A | 11/1980 | Matson et al. | |
| 4,427,772 A | 1/1984 | Kodera et al. | |
| 4,686,857 A | 8/1987 | Kato | |
| 4,808,287 A | 2/1989 | Hark | |
| RE32,920 E | 5/1989 | Matson et al. | |
| 4,992,156 A | 2/1991 | Silveri | |
| 5,019,250 A | 5/1991 | Lorenzen | |
| 5,221,444 A | 6/1993 | Silveri | |
| 5,233,860 A | 8/1993 | Mori et al. | |
| 5,240,228 A | 8/1993 | Silveri | |
| 5,251,656 A | 10/1993 | Sexton, Sr. | |
| 5,320,748 A | 6/1994 | Dupuis | |
| 5,331,966 A | 7/1994 | Bennett et al. | |
| 5,359,769 A | 11/1994 | Silveri | |
| 5,389,210 A | 2/1995 | Silveri | |
| 5,401,373 A | 3/1995 | Silveri | |
| 5,422,014 A | 6/1995 | Allen et al. | |
| 5,441,073 A | 8/1995 | Hoadley | |
| 5,474,664 A | 12/1995 | Thompson | |
| 5,545,310 A | 8/1996 | Silveri | |
| 5,580,438 A | 12/1996 | Silveri | |
| 5,616,239 A | 4/1997 | Wendell et al. | |
| 5,676,805 A | 10/1997 | Silveri | |
| 5,752,282 A | 5/1998 | Silveri | |
| 5,759,384 A | 6/1998 | Silveri | |
| 5,885,426 A | 3/1999 | Silveri | |
| 5,932,093 A | 8/1999 | Chulick | |
| 6,007,693 A | 12/1999 | Silveri | |
| 6,123,839 A | 9/2000 | Sussman | |
| 6,125,481 A | 10/2000 | Sicilano | |
| RE37,055 E | 2/2001 | Silveri | |
| 6,182,681 B1 | 2/2001 | Robertson et al. | |
| 6,238,555 B1 | 5/2001 | Silveri et al. | |
| 6,270,680 B1 | 8/2001 | Silveri et al. | |
| 6,309,538 B1 | 10/2001 | Kahn | |
| 6,340,431 B2 | 1/2002 | Kahn | |
| 6,426,629 B1 | 7/2002 | Edgson et al. | |
| 6,475,394 B2 | 11/2002 | Xiong | |
| 6,536,272 B1 | 3/2003 | Houston et al. | |
| 6,992,488 B2 | 1/2006 | Lin | |
| 7,056,664 B1 | 6/2006 | Hartwich et al. | |
| 7,189,314 B1 | 3/2007 | Pace et al. | |
| 7,328,624 B2 * | 2/2008 | Gysling | G01F 1/666 73/152.18 |
| 7,944,219 B2 | 5/2011 | Vincent | |
| 8,298,391 B2 | 10/2012 | Silveri | |
| 8,881,581 B2 | 11/2014 | Silveri | |
| 8,887,556 B2 | 11/2014 | Silveri | |
| 2001/0004962 A1 | 6/2001 | Hirota et al. | |
| 2001/0016682 A1 | 8/2001 | Berner et al. | |
| 2002/0014410 A1 * | 2/2002 | Silveri | C02F 1/008 204/412 |
| 2002/0070112 A1 | 6/2002 | Lee et al. | |
| 2002/0108911 A1 | 8/2002 | Xiong et al. | |
| 2002/0116042 A1 | 8/2002 | Boling | |
| 2003/0183538 A1 | 10/2003 | Lin | |
| 2003/1853538 | 10/2003 | Lin | |
| 2004/0138840 A1 | 7/2004 | Wolfe | |
| 2004/0211731 A1 | 10/2004 | Ferguson et al. | |
| 2006/0144704 A1 | 7/2006 | Ghesquiere et al. | |
| 2007/0006640 A1 * | 1/2007 | Gysling | G01F 1/36 73/61.44 |
| 2008/0017523 A1 | 1/2008 | Dietze | |
| 2009/0014329 A1 | 1/2009 | Silveri | |
| 2010/0111680 A1 * | 5/2010 | Binder | F04D 15/0066 415/177 |
| 2010/0148754 A1 | 6/2010 | Vincent | |
| 2012/0145561 A1 | 6/2012 | Coulon et al. | |

FOREIGN PATENT DOCUMENTS

| | | |
|---|---|---|
| JP | 2004053548 A | 2/2004 |
| JP | 2005181279 A | 7/2005 |
| WO | 2006007533 A1 | 1/2006 |
| WO | 2006031290 A1 | 3/2006 |
| WO | 2007096557 A1 | 8/2007 |

OTHER PUBLICATIONS

Kishkovich, O., Authorized Officer of of ISA/FIPS, "Notification of Transmittal of International Search Report and the Written Opinion of the International Searching Authority, or the Declarations," for International Application No. PCT/US2012/025125, 1 page, dated Jul. 26, 2012, 1 page.

Zhestovskaya, I., Authorized Officer of of ISA/FIPS, "PCT International Search Report," for International Application No. PCT/US2012/025125, 2 pages, dated Jul. 26, 2012.

Zhestovskaya, I., Authorized Officer of of ISA/FIPS, "Written Opinion of the International Searching Authority," for International Application No. PCT/US2012/025125, 4 pages, dated Jul. 26, 2012.

Instruction and operational and maintenance manual for chlorine sensor system, model SCLO3, www.etatron.com.ua. [cited in Jul. 26, 2012 International Search Report and Written Opinion for International Application No. PCT/US2012/025125], 7 pages total.

Description of Hach Ultra Polymetron liquid analyzer 9100, model 9186, registered on State Reg. No. 35858. [cited in Jul. 26, 2012 International Search Report and Written Opinion for International Application No. PCT/US2012/025125], 7 pages.

Five-Page Partial Translation of: Instruction and operational and maintenance manual for chlorine sensor system, model SCLO3, www.etatron.com.ua. [cited as Reference D2 in Jul. 26, 2012 International Search Report and Written Opinion for International Application No. PCT/US2012/025125].

Three-Page Partial Translation of: Description of Hach Ultra Polymetron liquid analyzer 9100, model 9186, registered on State Reg. No. 35858. [cited as Reference D3 in Jul. 26, 2012 International Search Report and Written Opinion for International Application No. PCT/US2012/025125].

Gangl, Martin, Supplementary European Search Report for European Patent Application No. EP 12 74 6823, dated Jun. 1, 2015, 9 pages.

Yokogawa, RC400G Residual Chlorine Analyzer FC400G Non-Reagent Free Chlorine Analyzer, 2005, 6 pages (as cited in Jun. 1, 2015 Supplementary European Search Report for European Patent Application No. EP 12 74 6823).

Yokogawa, RC400G Residual Chlorine Analyzer FC400G Non-Reagent Free Chlorine Analyzer, Bulletin 12F01A01-01E, 2005, 6 pages.

(56) References Cited

OTHER PUBLICATIONS

Patent Abstracts of Japan, Abstract for Japanese Publication No. 2000009677, Jan. 1, 2000, 1 page (cited in Jun. 1, 2015 Supplementary European Search Report for European Patent Application No. EP 12 74 6823).
Patent Abstracts of Japan, Abstract for Japanese Publication No. 2005181279, Jul. 7, 2005, 1 page (cited in Jun. 1, 2015 Supplementary European Search Report for European Patent Application No. EP 12 74 6823).
Machine Translation of JP-2000-009677, 11 pages.
Machine Translation of JP-2005-181279, 12 pages.
State Intellectual Property Office of the People's Republic of China, Search Report for Chinese Patent Application No. 2012800074396, dated Aug. 12, 2015, 2 pages.
Translation of: State Intellectual Property Office of the People's Republic of China, Search Report for Chinese Patent Application No. 2012800074396, dated Aug. 12, 2015, 2 pages.
Korean Intellectual Property Office, Office Action for Korean Patent Application No. 10-2013-7024093, dated Jun. 29, 2015, 5 pages.
Translation of: Korean Intellectual Property Office, Office Action for Korean Patent Application No. 10-2013-7024093, dated Jun. 29, 2015, 5 pages.

* cited by examiner

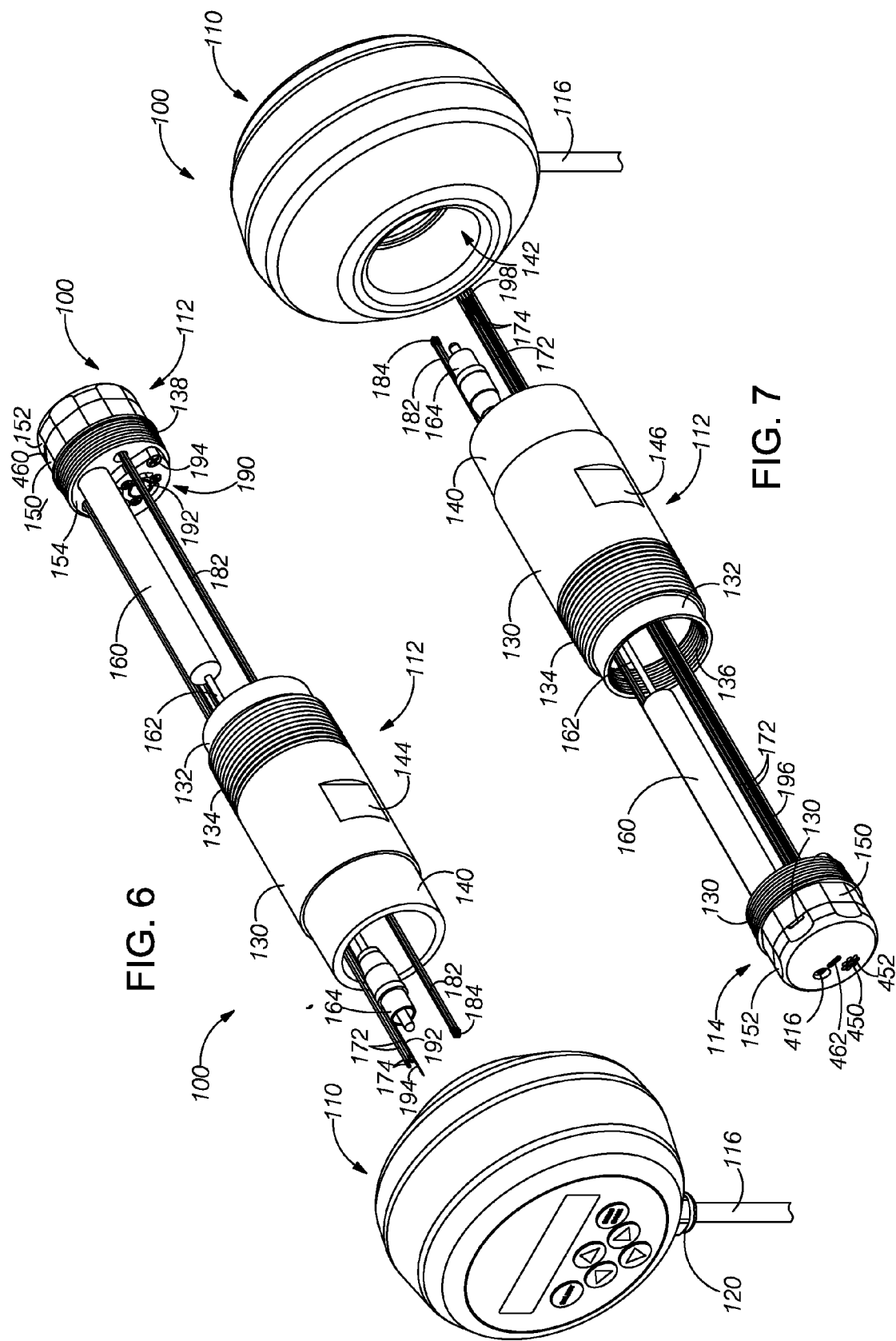

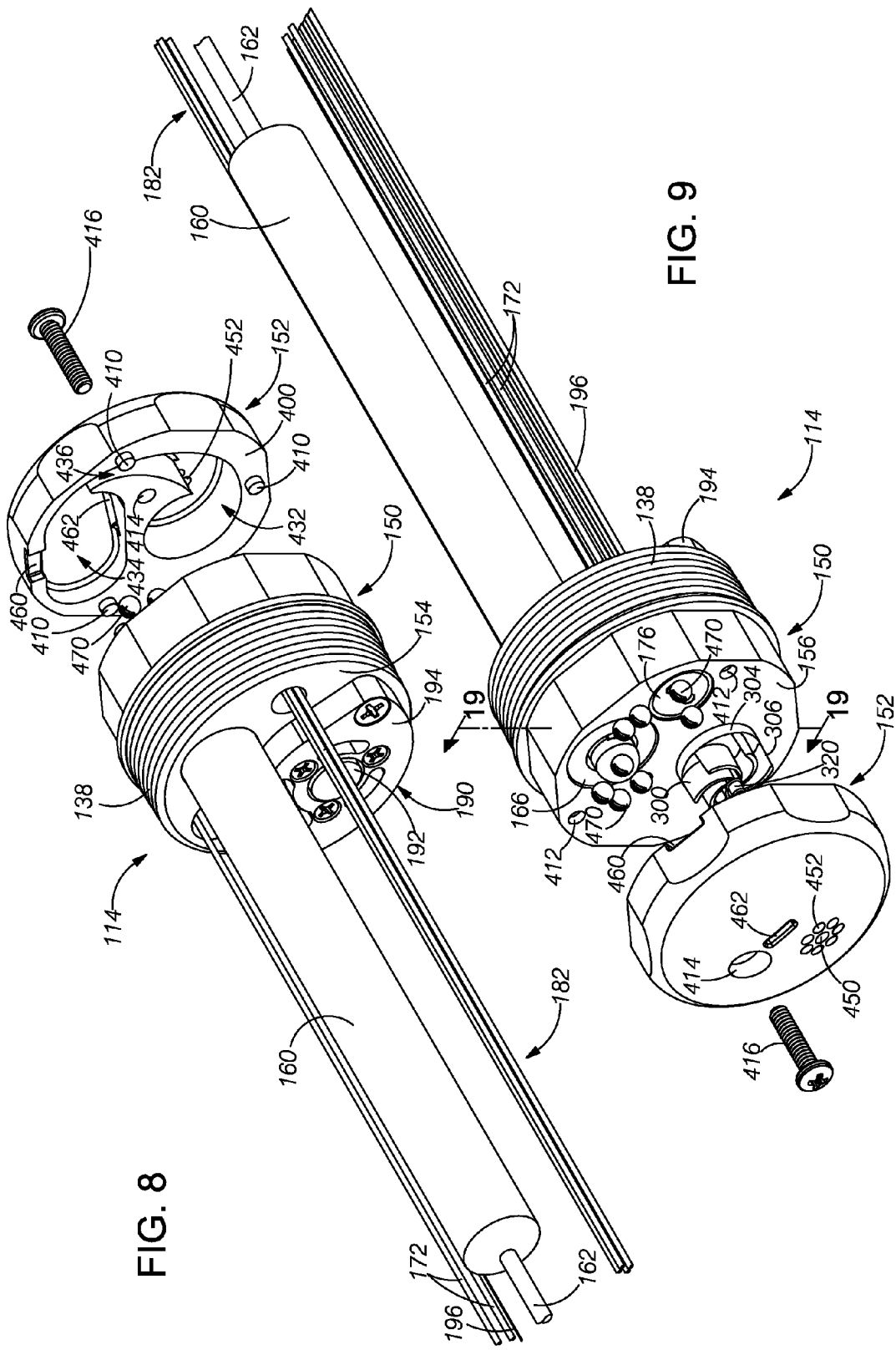

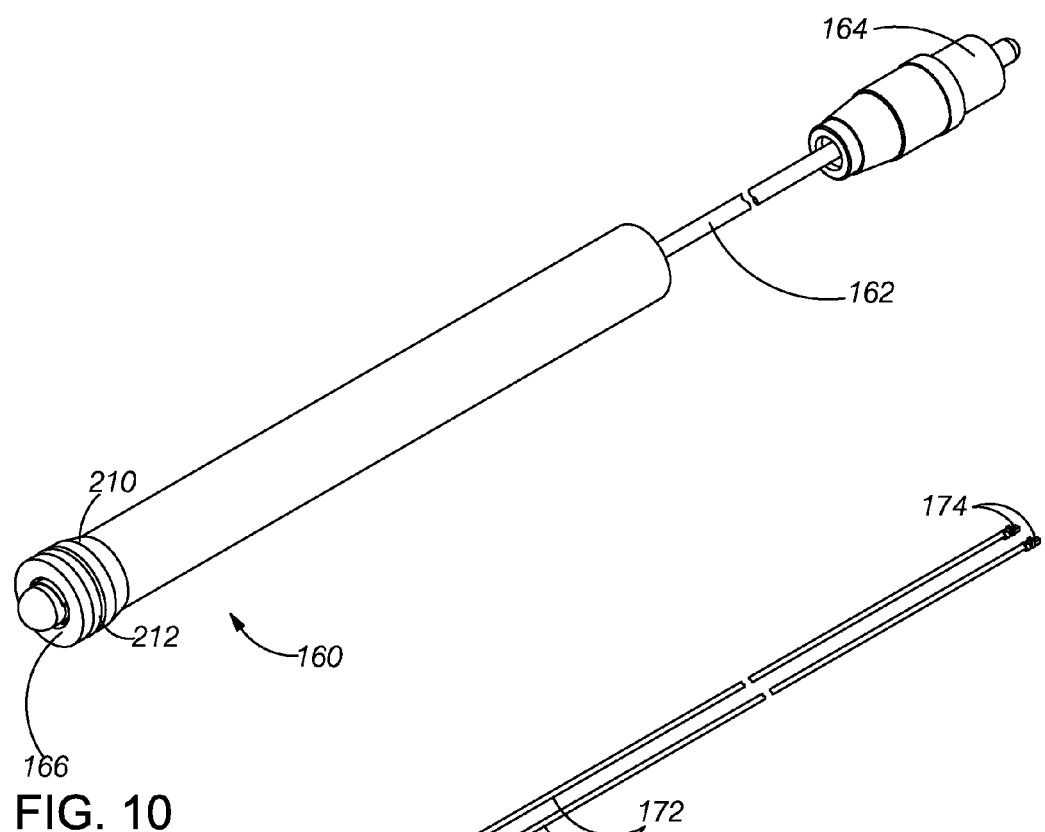
FIG. 10
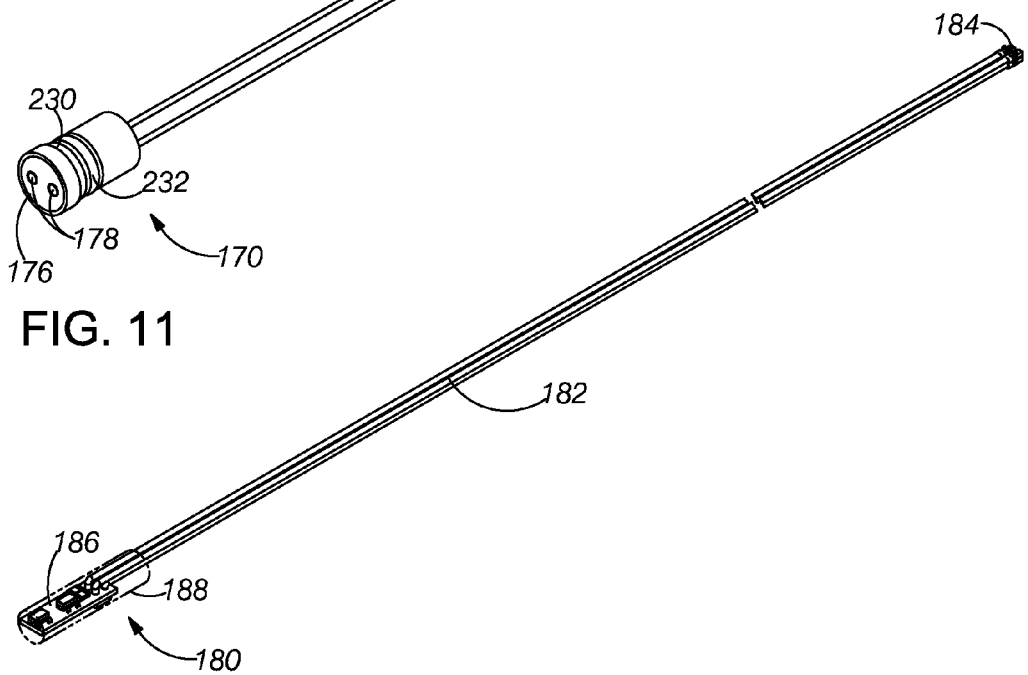
FIG. 11
FIG. 12

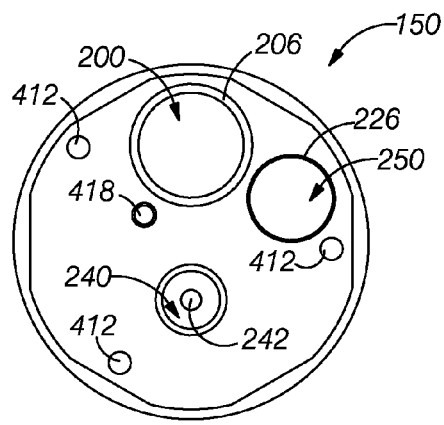
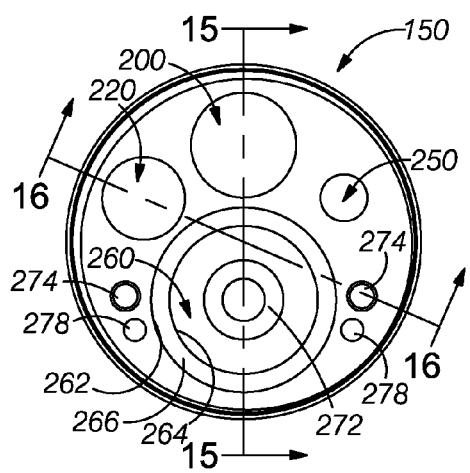
FIG. 13  FIG. 14
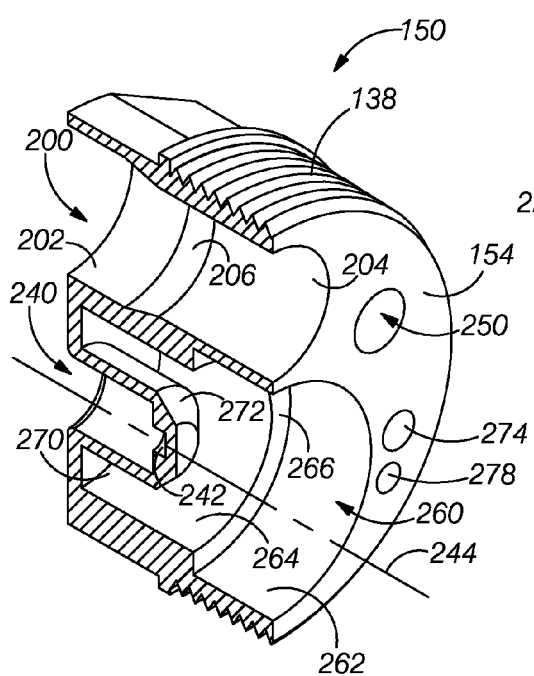
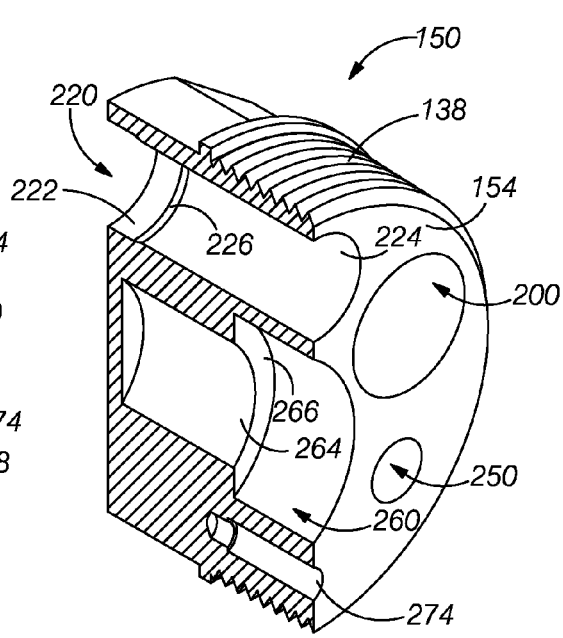
FIG. 15  FIG. 16

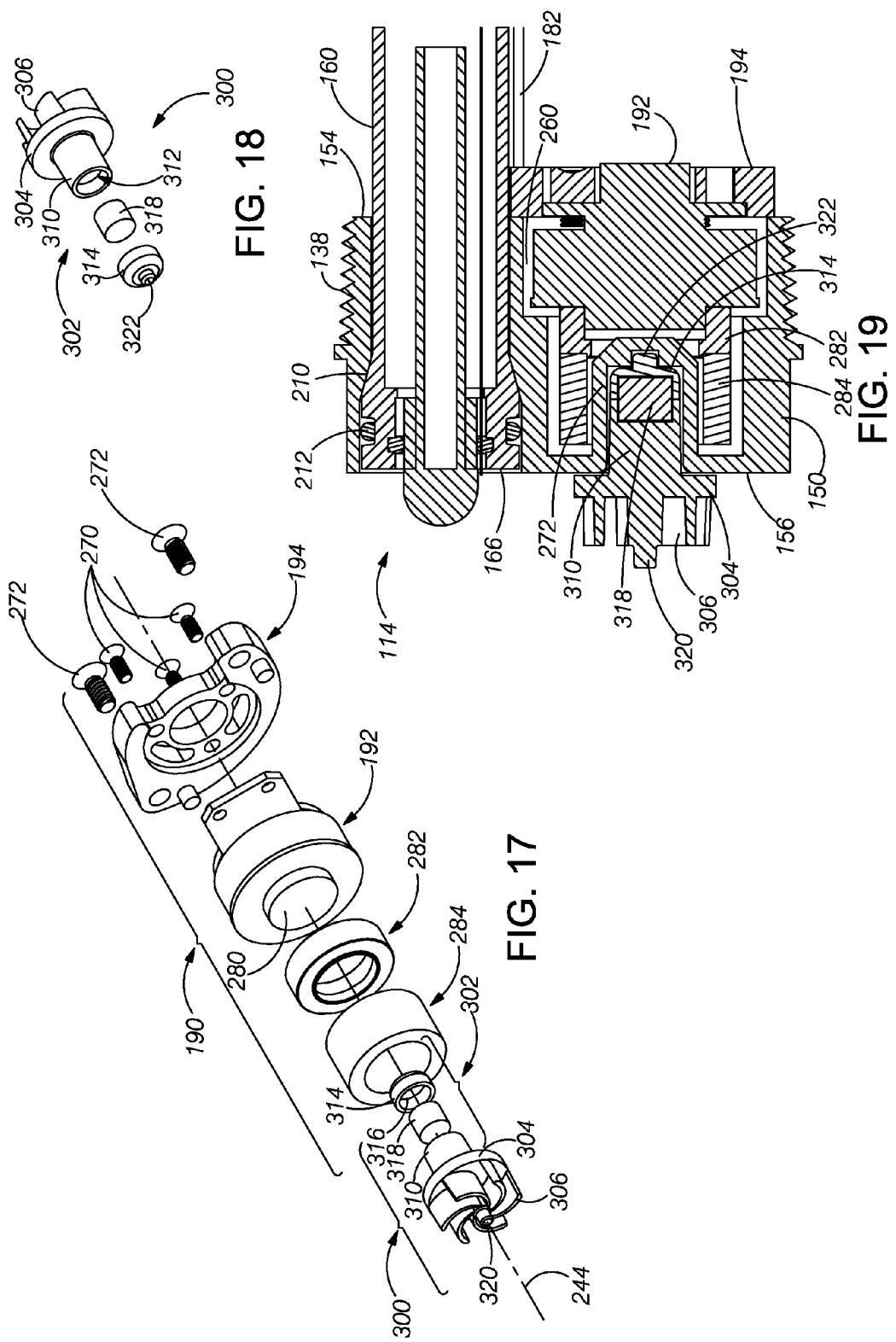

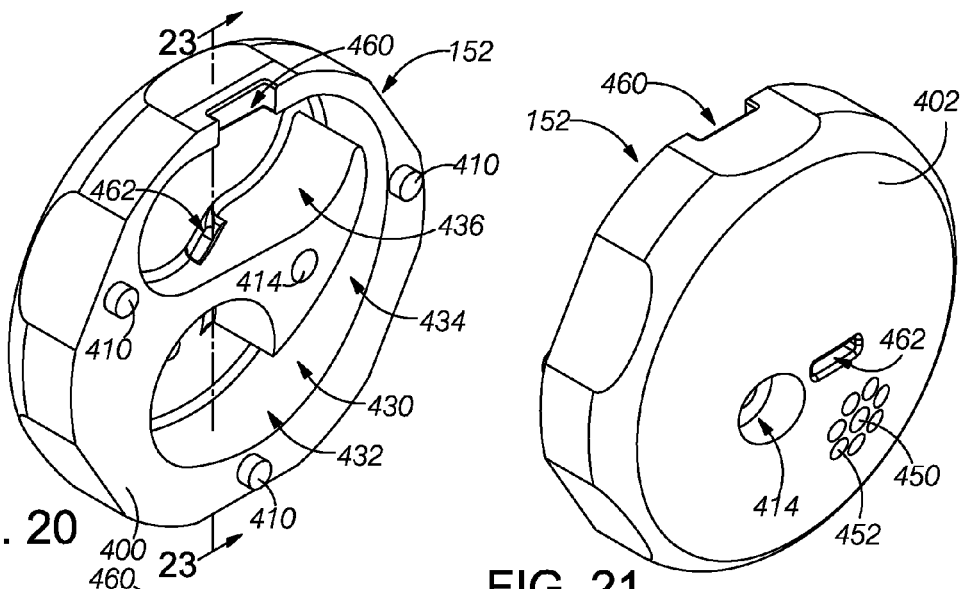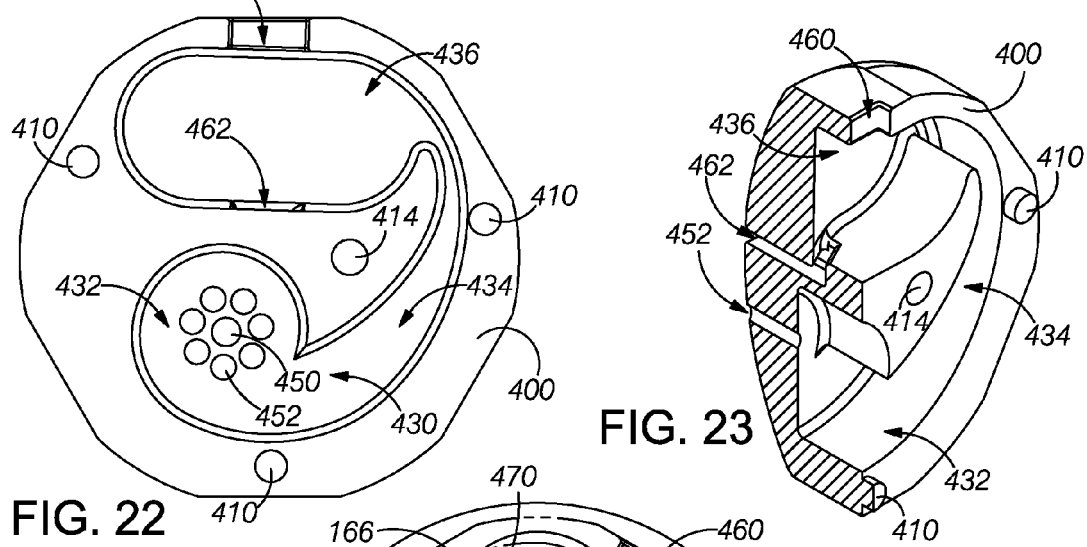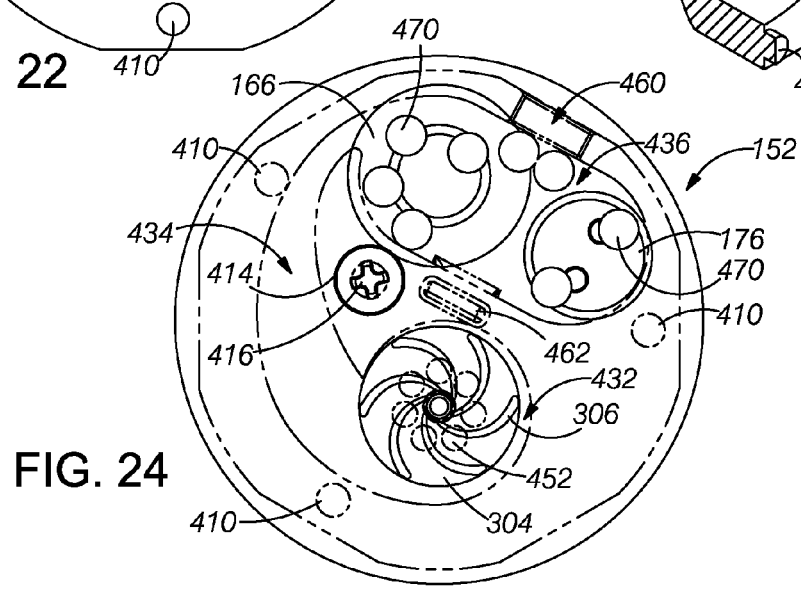

APPLIED DIFFERENTIAL VOLTAGE (SEA WATER)

APPLIED DIFFERENTIAL VOLTAGE (DRINKING WATER)

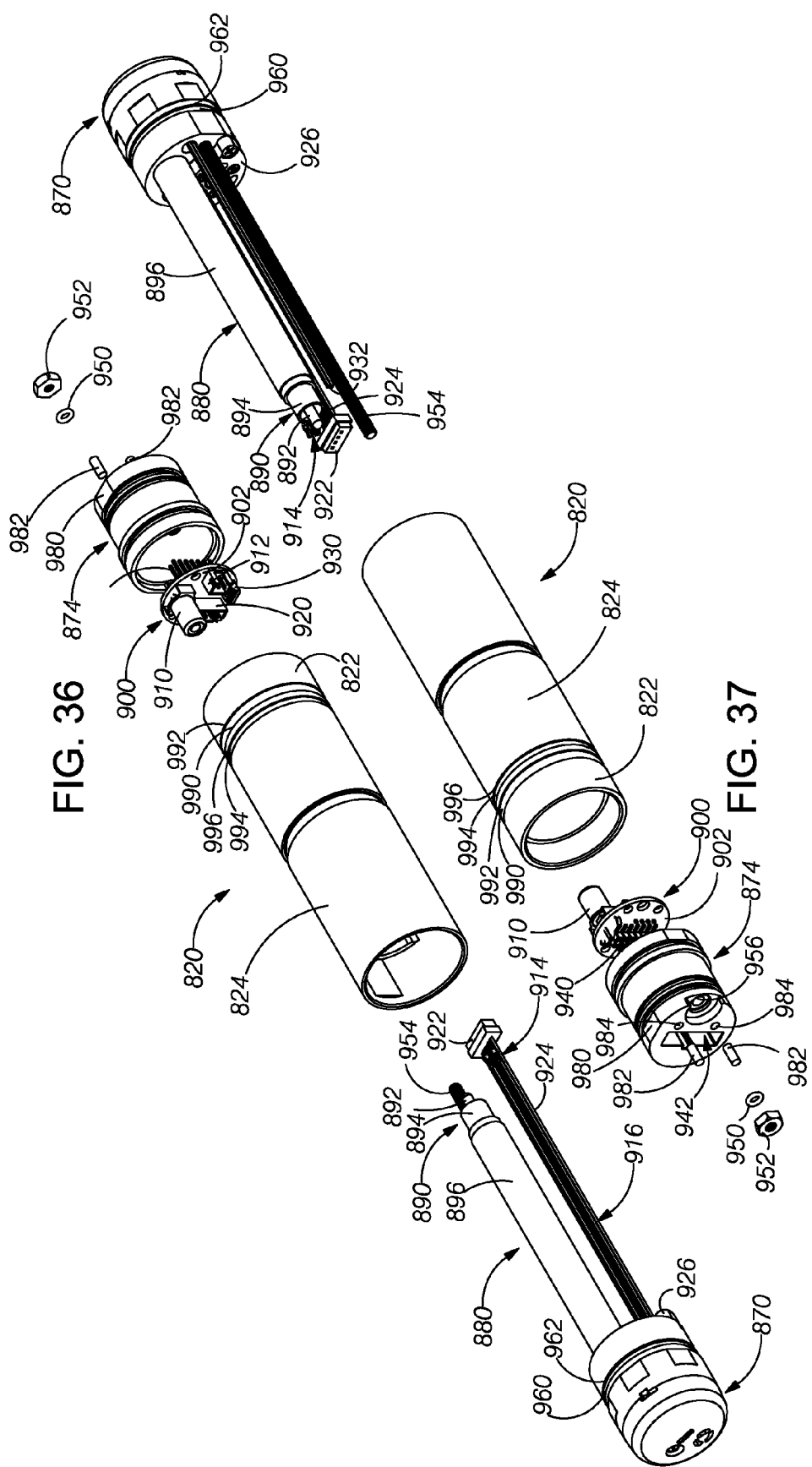

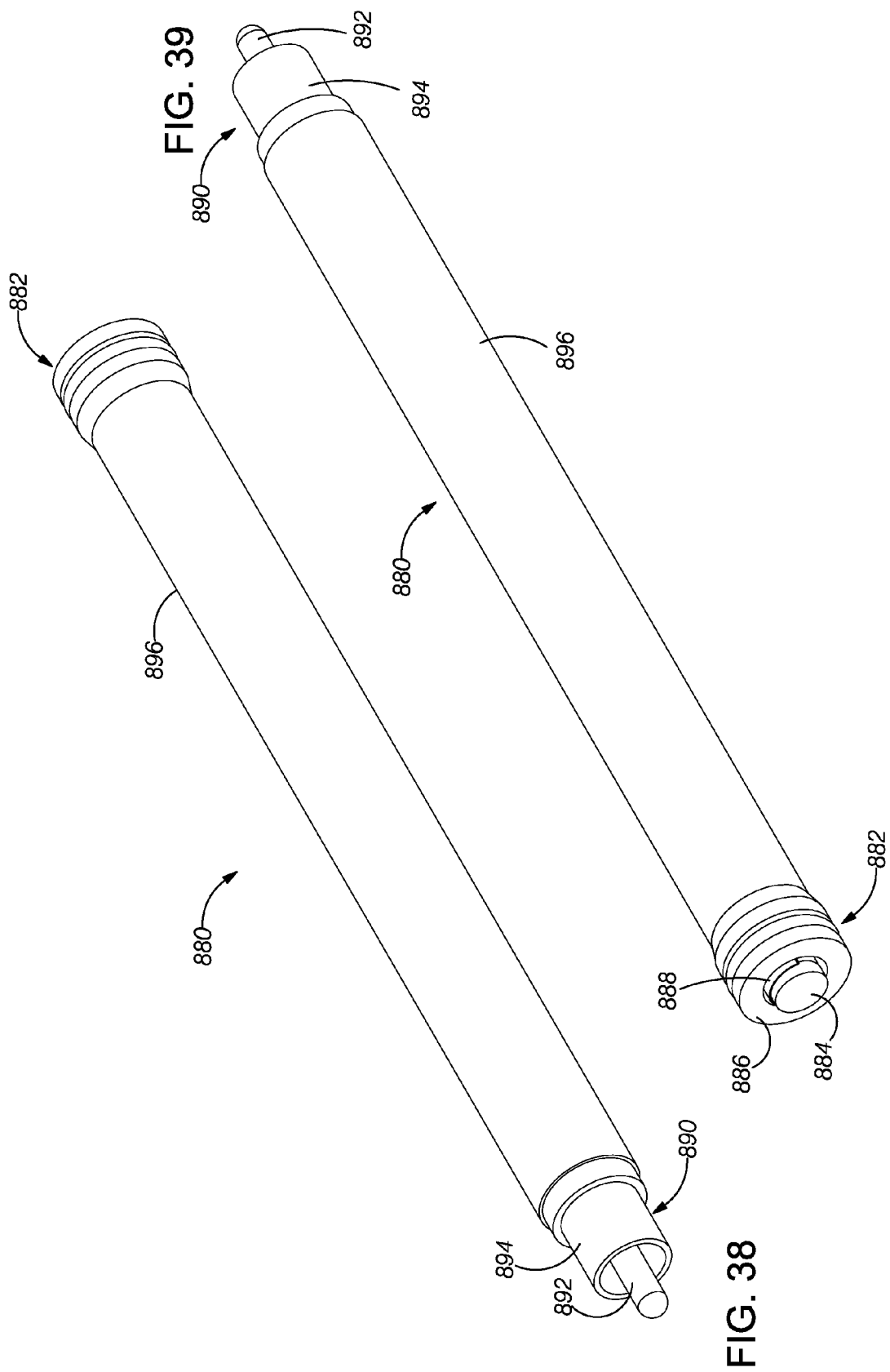

ic sensors.

AMPEROMETRIC SENSOR SYSTEM

RELATED APPLICATIONS

The present application is a divisional application of U.S. patent application Ser. No. 13/653,286 filed on Oct. 16, 2012, which is a divisional application of U.S. patent application Ser. No. 13/372,260 filed on Feb. 13, 2012, which claims the benefit of priority under 35 USC § 119(e) to U.S. Provisional Application No. 61/443,240, filed on Feb. 15, 2011, to U.S. Provisional Application No. 61/548,953, filed on Oct. 19, 2011, to U.S. Provisional Application No. 61/597,762, filed on Feb. 11, 2012, and to U.S. Provisional Application No. 61/597,832, filed on Feb. 12, 2012, which are incorporated by reference herein.

BACKGROUND OF THE INVENTION

Field of the Invention

The present invention is in the field of systems for testing water chemistry, and, more particularly, is in the field of amperometric sensors.

Description of the Related Art

Amperometric chlorine sensors are used in measuring chlorine residuals in drinking water, wastewater, cooling towers. Some newer applications are measurement of Total Residual Oxidant (TRO) in seawater. Recent regulatory actions require treatment of ballast water onboard ships to inactivate invasive species and prevent their discharge into non-native waters. Another new application is the measurement of up 500 ppm TRO in seawater used for biofouling back flushes of pretreatment microfiltration membranes used in Reverse Osmosis Desalination Systems.

A common problem encountered with online measurement of water chemistry in the field is fouled electrodes in the sensor system. Electrode measurements can be rendered unreliable when the working electrode is covered with either inorganic (salts such as calcium carbonate) layers or organic (biofouling) layers that inhibit electrode processes.

Another problem with certain sensors is the lack of a flow independent measurement method that can installed in a process flow without adverse effects from changing flow rates on the sensor signal. Amperometric sensors, in particular, are significantly affected by flow rates. Preferably, a sensor system should provide accurate measurements with flow rates ranging from 0 to more than 7 feet per second without an appreciable change in the sensor output signal. Another limitation of most sensors is the lack of an ability to directly insert a sensor into a process flow pipe or fitting for a simple installation such as may be necessary in a drinking water distribution system.

Maintenance costs of online chlorine monitors often greatly exceed the cost of the unit. Frequent recalibration is necessary with most, if not all, commercially available sensors due to changing electrode surface, fouling, electrolyte depletion, membrane fouling or stretching, pressure changes or spikes, flow changes and changes in pH.

Many sensor systems require a reagent feed of either an iodide solution or a buffer to lower the pH to 4.0. Other systems are dependent on flow or pressure and require controlled flow with a drain to waste to provide a constant flow rate to the sensor. This requirement further complicates the installation, maintenance and logistical requirements. This results in excessive water loss or unnecessary consumption. Solution consumption and replenishment result in higher costs and maintenance requirements.

Polarization of many sensors causes a loss of sensitivity over the first 2-24 hours, requiring recalibration. Sensitivity is reduced and the calibration changes if the sensor is removed and replaced.

When amperometric systems with exposed electrodes are used with even low levels of cyanuric acid (CYA), a polarization of the electrode occurs with a layer of CYA that inhibits electron processes, rendering the electrode unusable after less than one day of operation due to the low signal response.

Oxidation reduction potential (ORP) is often used for residual control and provides a qualitative indicator of sanitizer efficacy. The probes used for ORP sensing often suffer from a reduction in sensitivity caused by organics, particularly when high levels of cyanuric acid are present. An ORP sensor is needed that does not have this limitation.

The vast majority of commercial amperometric systems use membranes and electrolyte to control the reaction that occurs at the working (measurement) electrode. Problems with these systems are well known. Membranes stretch and foul with oil and organics and must be replaced frequently. Another problem with most of these systems is that they measure only hypochlorous acid, a free chlorine fraction, not free chlorine as measured by a DPD test kit. As a result, membrane sensors' signals change radically with a change in pH compared to bare electrode sensors. This results in a limited operational range of 6.0 to 8.0 pH. Beyond a pH of 8.0, the sensors produce very little signal, which can produce large errors.

Electrolyte must be replaced on an ongoing basis, often monthly. In addition to these deficiencies, membrane sensors are affected by flow and pressure changes requiring recalibration when either changes.

A known sensor uses a replaceable thin-film sensor formed on a substrate with multiple electrodes and a screen printed membrane on the working electrode for chlorine. The sensor has a very short life of approximately 6 months.

Another issue with known sensors is the detection and/or interference of chloramines in drinking water. Chloramine (monochloramine) is a disinfectant used to treat drinking water. Chloramine is most commonly formed when ammonia is added to chlorine to treat drinking water. The typical purpose of chloramine is to provide a longer-lasting residual for disinfection as the water moves through pipes to consumers. This type of disinfection is known as secondary disinfection. Chloramine has been used by water utilities for almost 90 years, and the use of chloramine is closely regulated. More than one in five Americans uses drinking water treated with chloramine. Water that contains chloramine and that meets EPA regulatory standards is safe to use for drinking, cooking, bathing and other household uses.

Many utilities use chlorine as a secondary disinfectant; however, in recent years, some utilities have changed the secondary disinfectant to monochloramine to meet disinfection byproduct regulations.

Monochloramine ($NH_2Cl$) is commonly used in low concentrations as a secondary disinfectant in municipal water distribution systems as an alternative to free chlorine chlorination. The use of monochloramine is increasing. Chlorine (sometimes referred to as "free chlorine") is being displaced by monochloramine, which is much more stable and does not dissipate from the water before it reaches consumers. Monochloramine also has a very much lower, however still present, tendency than free chlorine to convert organic materials into chlorocarbons such as chloroform. Such compounds have been identified as carcinogens; and in 1979 the United States Environmental Protection Agency began regulating levels of such compounds in drinking water. Furthermore, water treated with chloramine lacks the distinct chlorine odor of the gaseous treatment and so has improved taste. In swimming pools, chloramines are formed by the reaction of free chlorine with organic substances. Chloramines, compared to free chlorine, are both less effective as a sanitizer and more irritating to the eyes of swimmers. When swimmers complain of eye irritation from "too much chlorine" in a pool, the problem is typically a high level of chloramines. Some pool test kits designed for use by homeowners are sensitive to both free chlorine and chloramines, which can be misleading.

The following chart illustrates the current versus the Cl potential and versus the monochloramine potential that is used to determine which species is present:

|  | Analytical Signal (µA) | | | | Analytical Signal (µA) (corr.) | |
| --- | --- | --- | --- | --- | --- | --- |
| Potential (V) | Chlorine | Blank | $NH_2Cl$ | Blank | Chlorine | $NH_2Cl$ |
| 0.30 | 1.179 | 0.016 | 0.034 | 0.008 | 1.162 | 0.026 |
| 0.20 | 1.400 | 0.016 | 0.009 | 0.004 | 1.383 | 0.005 |
| 0.10 | 1.6595 | 0.027 | 0.248 | 0.028 | 1.633 | 0.220 |
| 0.00 | 2.287 | 0.241 | 0.745 | 0.311 | 2.046 | 0.434 |

In the foregoing chart, the concentration of Cl is 20 parts per million (ppm), and the concentration of $NH_2Cl$ is 20.5 ppm as Cl. The "blank" readings in the two columns are determined by measuring a known liquid with 0 concentration of chlorine or monochloramine. The corrected analytical signals for chlorine and monochloramine are determined by subtracting the blank values from the measured values at each applied potential. The data points for the corrected analytical signals versus the potential voltage are plotted in the graph shown in FIG. 40.

The following chart illustrates the ratios of the analytical signals for corresponding ratios of the potentials:

| Ratios of Corrected Analytical Signals (µA) versus ratios of potentials (V) | | |
| --- | --- | --- |
| Ratios (V) | Chlorine (corrected) | $NH_2Cl$ (corrected) |
| 0.10:0.30 | 1.40 | 8.578 |
| 0.00:0.30 | 1.76 | 16.913 |

As can be seen from the foregoing data, it is possible to determine whether the species is monochloramine or free chlorine by the ratio of the measurement of two potentials. A ratio of greater than 5 indicates that the species is monochloramine. A display icon can be used to indicate that monochloramine is present to thereby invite the use to perform an action. For example, when used with a swimming pool, the icon may warn the operator that the water needs to be superchlorinated or that a non-chlorine shock compound needs to be added to lower the monochloramine level.

The data also illustrates the dramatic difference in signals produced by similar levels of free chlorine and monochloramine. Two stored calibrations can be used—one for free chlorine and one for total chlorine. The ratio can also be used to quantify the monochloramine and free chlorine fractions based on the magnitude of the ratio. The stored calibrations can be adjusted to read out in parts per million (ppm) of monochloramine if monochloramine is present. In a drinking water application, the residual displayed can be adjusted to display ppm monochloramine instead of free chlorine to more accurately display the chlorine level. Otherwise, the sensor system may drastically under report the sanitizer levels due to the lower signal response of monochloramine.

SUMMARY OF THE INVENTION

An amperometric system with low maintenance requirements is needed. The system should be able to operate for extended periods unattended. The system should operate for extended periods (e.g., for up to a year) without a sensor replacement or other maintenance. Preferably, the chlorine sensor and the pH sensor should be replaceable individually to reduce the cost of operation. Preferably, the sensor incorporates a method of overcoming the polarization effects of cyanuric acid (CYA). The sensor should not require frequent recalibration, and if a sensor is removed or replaced, a sensor should quickly stabilize and report reliable readings.

An aspect of embodiments in accordance with the present invention is a sensor system that provides a reliable sensor platform that has a long lived chlorine sensor, provides a replaceable pH sensor and requires only infrequent calibration. The sensor system provides fast measurement response times, is largely unaffected by changes in flow, pH, temperature or conductivity, and is capable of direct insertion in a pipe. The sensor is resistant to biofouling and to high levels of water hardness, which makes the sensor practical for use in the most challenging applications including seawater and wastewater as well as in cleaner applications for the measurement of chlorine in drinking water.

The sensor system disclosed herein can be used with either a flow cell that receives a constant flow rate of water or an integrated pump version that can be operated independent of the flow rate and is capable of direct pipe insertion.

An embodiment of the sensor system includes cleaning balls, which are moved by the flow from either the pump or the water supplied to the flow cell to abrade the surface of the electrodes and the pH sensor to remove salts that build up as a result of water hardness and in some cases oxide formation. Preferably, the sensor system uses polytetrafluoroethylene (PTFE) (e.g., Teflon® resin) balls or other polymeric balls to simultaneously clean scale from both the pH and the reference electrodes and from the auxiliary electrode and the working electrode for the chlorine sensor. In some cases, it is preferable to use PEEK (polyether ether ketone) balls in a seawater oxidant sensor. The flow cell is advantageously designed so that the balls cannot escape during normal operation. An inlet port is substantially smaller than the ball diameter, which prevents ball egress when the flow is discontinued and sensor is removed. A small clearance between the sensor and the walls of the flow cell prevent balls from escaping via the outlet port of the flow cell. The housing is configured so that captured air can be purged during operation. In particular, the outlet port is positioned above the sensor end when the sensor system is inserted into the horizontally oriented pipe fitting. The position of the outlet port enables air to egress the flow cell.

In accordance with another embodiment of a self-cleaning sensor having an integral pump, the sensor provides a consistent reading with varying rates of flow from 0 to 7 feet per second (FPS). The sensor is self-cleaning under challenging conditions. The sensor provides a higher sensitivity signal due to the higher velocity across the electrodes developed within the sensor cover by the integral pump. The integral pump provides a consistent flow across the chlorine electrodes. The sensor cleans all three electrodes simultaneously. The sensor also cleans the pH sensor glass. The sensor is integrated to provide automatic pH compensation. The sensor has long-life electrodes.

In the sensor, a magnetically coupled impeller is rotated by a motor that produces a water flow across the electrodes with a generally constant flow velocity. This flow rate also improves the electrode sensitivity to chlorine with higher velocity across the electrodes. A cover retains the balls and forms a pump volute to produce the flow and move the balls to abrade the electrode surfaces and interior portion of the sensor to remove scale and biological coatings. In a preferred embodiment, the motor is a 3-phase brushless DC (BLDG) motor that has low noise and that requires low current. The pump is a self-priming. The pump includes an integrated tachometer to detect motor movement and to control motor speed.

In preferred embodiments, the wetted portions of the sensor that are subject to biofouling are manufactured from PTFE or Ultra High Molecular Weight Polyethylene (UHMW) (e.g., Teflon® resin) and are resistant to adhesion of organic gels and microorganisms. The sensor has a hemispherical shape, which allows the release of large particulates when the sensor is installed in a plumbing tee and subject to a flowing stream across the immersed sensor.

In preferred embodiments of the sensor, a negative potential is applied to the electrodes subsequent to the application of the measurement potential. The application of the negative potential provides an unanticipated benefit of preventing the passivation of the electrode when cyanuric acid (CYA) is present. In the absence of the subsequently applied negative potential, the electrode is rapidly passivated such that within approximately 24 hours, the signal from the sensor drops by approximately 90% and thus no longer correlates with the chlorine level being measured. The subsequently applied negative potential minimizes the effects of polarization by preventing the gradual loss of sensitivity, which enables indefinitely repeatable measurements.

The sensor system disclosed herein includes a long-life chlorine sensor, which may have different configurations. In one advantageous configuration, the chlorine sensor comprises a platinum working electrode and a platinum auxiliary electrode. In another advantageous configuration, the chlorine sensor comprises a platinum auxiliary electrode and a gold working electrode. The platinum electrode may comprise an alloy of platinum. The gold electrode may comprise an alloy of gold. In another configuration, both electrodes are platinum. In another configuration, both electrodes are gold. Preferably, the chlorine sensor is enclosed within a housing comprising polyether ether ketone (PEEK), a semi-crystalline thermoplastic having excellent mechanical properties, including hydrophobicity and chemical resistance properties. Alternatively UHMW may be used.

When using two platinum electrodes to measure seawater or water in swimming pools having cyanuric acid, a measurement potential of approximately 0.25 volt is applied for approximately 30 seconds. The measurement potential is followed by a potential of −2.0 volts applied for approximately 5 seconds. When using gold electrodes to measure drinking water and waste water, a measurement potential of approximately 0.25 volt is applied for approximately 5 to 30 seconds, followed by a potential of −0.6 volts applied for approximately 1 to 10 seconds. When using platinum electrodes to measure drinking water and waste water, a measurement potential of approximately 0.25 volt to approximately 0.4 volts is applied for approximately 5 to 30 seconds, followed by a potential of −0.6 volts applied for approximately 1 to 5 seconds. The results of measurements using the sensor disclosed herein and the results of DPD spectrophotometric measurements are comparable.

Since the same sensor may be used in several different applications with different water make up, certain parameter settings such as measurement time and potentials may be optimized for each water type. With one menu selection, the user can select the water type and the parameter settings are changed. This feature simplifies operation and facilitates use of the sensor in different applications with the single sensor optimized for a certain water type. For example, in one embodiment, "seawater" can be selected or "drinking water" can be selected.

The sensor sequentially measures several water parameters in addition to chlorine, including ORP, pH and conductivity. The ORP measurement can be performed in a very short interval of 5 seconds. The cycling between measurements impresses a potential that prevents absorption of organics on the electrode surface. To speed up equilibration of the ORP measurement, the potential is set to 0.0 Volts before the start of the ORP measurement. This enables rapid, reliable ORP measurements in challenging water conditions.

The sensor system disclosed herein includes a replaceable pH sensor, which may be a single-junction sensor or a double-junction sensor. In preferred embodiments, the pH sensor is a double-junction sensor or a differential style pH sensor. Alternatively, a solid-state reference electrode may be substituted for the pH sensor in applications where pH measurement is unnecessary. For example, the pH of seawater is fairly constant and generally does not need to be measured. The use of the solid reference electrode eliminates the fragile glass bulb required with most pH sensors and enables long life and low maintenance requirements. Each of the reference/pH cartridges may be used with only a single change made by the user with the software interface.

The sensor system disclosed herein includes a pump having a volute cover. The pump includes an impeller that moves a plurality of cleaning balls that remove scale and other contaminants from the electrodes. Preferably, the cleaning balls comprise Teflon® resin; however, the cleaning balls may comprise ceramic, glass or other suitable materials. The impeller is coupled to a motor by diametrically magnetized magnets. In certain preferred embodiments, the diametrically magnetized magnets are neodymium magnets.

Preferably, the sensor system disclosed herein includes an integrated temperature sensor and a memory device on a printed circuit board (PCB). In certain embodiments, the temperature sensor is potted into the sensor housing using a thermally conductive epoxy. In particularly preferred embodiments, the sensor body wall has a thickness of approximately 0.03 inch to minimize the thermal time constant from the fluid being measured to the temperature system. The memory device, which is preferably an electrically erasable programmable read only memory (EEPROM), stores calibration values for the sensor system and the serial number of the sensor system.

An aspect in accordance with embodiments disclosed herein is a sensor system for measuring at least one parameter of water. The sensor system comprises an electronics subsystem and a sensor housing. The sensor housing is electrically and mechanically coupled to the electronics subsystem. The sensor housing comprises a chamber that receives water via at least one inlet and that releases water via at least one outlet. At least one sensor within the sensor housing has at least one electrode exposed to water in the chamber. A flow generator causes water to flow through the chamber.

Preferably, the sensor housing is configured to be inserted into a pipe carrying the water for which the parameter is to be measured.

Preferably, the flow generator is a pump that comprises a motor and an impeller. The sensor housing comprises a wet side exposed to water and a dry side isolated from water. The motor is mounted on the dry side of the sensor housing; and the impeller is mounted on the wet side of the sensor housing. The impeller is magnetically coupled to the motor such that rotation of the motor on the dry side of the housing rotates the impeller on the wet side of the housing. In certain embodiments, the motor comprises a brushless DC motor.

In an illustrated embodiment, the sensor system is an amperometric sensor system.

Preferably, the sensor system further comprises a plurality of movable objects constrained within the chamber and movable by water flowing in the chamber to impinge upon and clean a surface of the at least one electrode. For example, the movable objects may comprise glass spheres or may comprise polytetrafluoroethylene (PTFE) spheres. Preferably, the movable objects have dimensions sufficiently larger than the at least one inlet and the at least one outlet such that the movable objects are confined to the chamber.

In certain embodiments of the system, the at least one sensor comprises at least three electrodes, and the at least three electrodes are cleaned simultaneously by a plurality of movable objects moving within the chamber as water flows through the chamber.

In certain embodiments of the system, the at least one electrode comprises the electrodes in a chlorine sensor and the electrodes in a pH sensor wherein the electrodes in the chlorine sensor and the electrodes in the pH sensor are cleaned simultaneously. Preferably, the at least three electrodes are cleaned simultaneously by a plurality of movable objects within the chamber as water flows through the chamber.

In certain embodiments of the system, the at least one outlet of the chamber is positioned so that any air in the chamber exits through the at least one outlet.

Another aspect in accordance with embodiments disclosed herein is an amperometric sensor system for measuring at least one parameter of water. The sensor comprises at least one sensor probe positioned in fluid communication with water having the parameter to be measured. The probe comprises a plurality of electrodes. The sensor generates an output signal responsive to the concentration of the parameter to be measured. A control system electrically coupled to the sensor probe applies differential voltages between at least a first electrode of the plurality of electrodes and a second electrode of the plurality of electrodes. The control system is configured to generate a first differential measuring voltage in a range between −0.2 volt and +0.5 volt between the first electrode and the second electrode, and to generate a second differential measuring voltage between 0 volt and −5 volts between the first electrode and the second electrode. The second differential measuring voltage is applied for a duration of at least 0.1 second following the first differential measuring potential.

In certain embodiments of the system, the first electrode and the second electrode each comprise platinum. Preferably, the first electrode and the second electrode are planar electrodes deposited on a nonconductive substrate. For example, the sensor system is configured for use with water that includes Cyanuric acid.

In certain embodiments of the system, at least one of the first electrode and the second electrode comprises gold.

In certain embodiments of the system, the sensor system is configured for use with water comprises seawater.

In certain embodiments of the system, the sensor system is configured for use with water includes greater than 1,000 parts per million (ppm) of sodium chloride.

Another aspect in accordance with embodiments disclosed herein is a method for quantifying two species in water. The method comprises applying a first differential measurement potential between at least first and second electrodes of at least one sensor probe; and measuring a first output signal responsive to the concentration of a parameter of water to be measured and responsive to the first differential measurement potential. The method further comprises applying a second differential measurement potential between the at least first and second electrodes of the at least one sensor probe, where the second differential measurement potential is different from the first differential measurement potential. The method further includes measuring a second output signal responsive to the concentration of the parameter of water to be measured and responsive to the second differential measurement potential. The method further includes determining a ratio of the first output signal to the second output signal; and determining which of the two species is present based on the ratio of the first output signal to the second output signal. The method then calculates and quantifies the species determined to be present. In certain embodiments of the method, when both species are present, the method quantifies each species according to the ratio of the first output signal to the second output signal. In certain aspects of the method, the first species comprises free chlorine and the second species comprises chloramine; and the ratio of the first output signal to the second output signal has a value in a first range when the species in the water comprises free chlorine and has a value in a second range when the species in the water comprises chloramine.

Another aspect in accordance with embodiments disclosed herein is a multi-use sensor system for sensing pH in water. The sensor system comprises an electronics base unit that houses electronics circuitry common to a plurality of sensor applications. The sensor system further comprises a removable sensor cartridge that houses at least one replaceable pH sensor, wherein the replaceable pH sensor in the removable sensor cartridge is configured to be one of (1) a differential pH sensor, (2) a combination pH sensor and reference electrode, or (3) a reference' only sensor.

In certain embodiments of the multi-use sensor system, the replaceable pH sensor has a first sensing end having a flared body portion and has a second connecting end having a sensor connector fixed thereon. The replaceable pH sensor has a fixed length between the flared body portion and the sensor connector. The removable sensor cartridge includes a flared cavity configured to receive the flared body portion of the replaceable pH sensor and has a mating connector configured to mate with the sensor connector. The mating connector is positioned to electrically and mechanically engage the sensor connector when the flared body portion of the replaceable pH sensor is positioned within the flared cavity.

Another aspect in accordance with embodiments disclosed herein is a method for preventing polarization of electrodes when measuring oxidation reduction potential (ORP) using the electrodes. The method comprises impressing a voltage potential between two electrodes of a sensor for a first predetermined time. The method further comprises removing the voltage potential between the two electrodes of the sensor for a second predetermined time and measuring ORP. The method further comprises repeating the impressing and removing actions for respective first predetermined times and second predetermined times, wherein impressing the voltage potential and removing the voltage potential prevents polarization of the electrodes.

In certain embodiments of the method, a total time of the first predetermined time followed by the second predetermined time is less than one minute.

Another aspect in accordance with embodiments disclosed herein is a reconfigurable amperometric sensor having first and second electrodes to measure at least one parameter of water, wherein a type of water in which the parameter is measured can be one of drinking water, seawater and pool water. The amperometric sensor comprises a selector for selecting the type of water in which the at least one parameter of the water is to be measured. A means responsive to the selector configures the amperometric sensor in accordance with the type of water selected to vary at least one operating parameter in accordance with a preset set of operating parameters for each type of water. The operating parameters include a measurement time during which a first voltage potential is applied between the first and second electrodes to measure the at least one parameter of the water and further include a magnitude of a second voltage potential applied by the sensor during a non-measurement time to prevent polarization caused by the first voltage potential.

Another aspect in accordance with embodiments disclosed herein is a method of cleaning an amperometric sensor having a plurality of electrodes positioned on the face of a sensor body. Each of the plurality of electrodes has a surface exposed to water having at least one parameter to be measured by the plurality of electrodes. The method comprises confining a plurality of movable objects in a cavity that comprises a volume of water exposed to the surfaces of the plurality of electrodes. The method further comprises flowing water into, through and out of the cavity to cause the water to flow across the surfaces of the plurality of electrodes. The method further comprises circulating the plurality of movable objects within the cavity to cause the plurality of movable objects to impinge on the surfaces of the plurality of electrodes as the water flows through the cavity. The plurality of movable objects abrade the surfaces of the plurality of electrodes to thereby clean the electrodes.

In certain embodiments of the method, the movable objects are spherical. In certain embodiments of the method, the movable objects comprise glass. In certain embodiments of the method, the movable objects comprise polytetrafluoroethylene (PTFE).

In certain embodiments of the method, a control system electrically coupled to the sensor probe applies differential voltages between at least a first electrode of the plurality of electrodes and a second electrode of the plurality of electrodes. Preferably, the control system generates a first differential measuring voltage in a range between −0.2 volt and +0.5 volt between the first electrode and the second electrode, and generates a second differential voltage between 0 volt and −5.0 volts between the first electrode and the second electrode. The second differential voltage is applied for a duration of at least 0.1 second following the first differential measuring potential.

In certain embodiments of the method, the water is seawater and the oxidant levels measured are between 1 and 500 ppm.

Another aspect in accordance with embodiments disclosed herein is a method of prevention of passivation in an amperometric sensor system. The method comprises positioning at least one sensor probe in fluid communication with water having a parameter to be measured. The probe comprises a plurality of electrodes. The sensor generates an output signal responsive to the concentration of the parameter to be measured. The method further comprise electrically coupling a control system to the sensor probe to apply differential voltages between at least a first electrode of the plurality of electrodes and a second electrode of the plurality of electrodes. The control system is configured to generate a first differential measuring voltage in a range between −1.0 volt and +0.5 volt between the first electrode and the second electrode, and to generate a second differential voltage between 0 volt and −5.0 volts between the first electrode and the second electrode. The second differential voltage is applied for a duration of at least 0.1 second following the first differential measuring potential.

In certain embodiments of the method, the water includes cyanuric acid.

In certain embodiments of the method, the water is seawater, and the parameter to be measured is an oxidant in the seawater. In such embodiments, the plurality of electrodes includes a solid-state reference electrode and the surface of at least one of the electrodes is coated with platinum.

Another aspect in accordance with embodiments disclosed herein is a method of operating an amperometric sensor having a plurality of electrodes positioned on the face of a sensor body. Each of the plurality of electrodes has a surface exposed to water having at least one parameter to be measured by the plurality of electrodes. The method comprises positioning the surfaces of the plurality of electrodes in a cavity that comprises a volume of water. The method further comprises operating a flow generator to flow the water having the at least one parameter to be measured into, through and out of the cavity to cause the water to flow across the surfaces of the plurality of electrodes at a substantially constant velocity. The method further comprises measuring the at least one parameter of the water while the water is flowing across the surfaces of the plurality of electrodes.

In certain embodiments of the method, the flow generator comprises an impeller and comprises a motor to impart rotation to the impeller. The method further comprises positioning the impeller in the cavity to expose the impeller to the water in the cavity, and positioning the motor outside the cavity in a location isolated from the water. The motor is mechanically coupled to a first rotatable coupling device outside the cavity. Energy is applied to the motor to rotate the first rotatable coupling device. The first rotatable coupling device is magnetically coupled to the impeller within the cavity to cause the impeller to rotate within the cavity. In the illustrated embodiment, the motor has a motor torque. The first rotatable coupling device is coupled to the impeller with at least a minimum coupling force, wherein the minimum coupling force selected to be greater than the motor torque so that the motor will not rotate the first coupling device if the impeller cannot rotate.

Another aspect in accordance with embodiments disclosed herein is a method for reducing build-up of contamination on a sensor. The method comprises positioning a surface of a sensor in an enclosure having at least one inlet to allow water to enter the enclosure and having at least two outlets to allow water to exit the enclosure. The enclosure contains a plurality of movable particles. The movable particles have dimensions selected to prevent the movable particles from passing out of the enclosure via the outlets. The method further comprises flowing water within the enclosure from the inlet to the outlets to cause the water to flow over the surface of the sensor. The flow of the water causes at least some of the movable particles to impinge on the surface of the sensor to dislodge contamination from the surface of the sensor. The outlets are oriented with respect to a direction of flow of the water to inhibit the movable particles from blocking the at least two outlets.

Another aspect in accordance with embodiments disclosed herein is an apparatus. The apparatus comprises an enclosure that houses a surface of a sensor adapted to measure a characteristic of water. The enclosure has at least one inlet to allow water to enter the enclosure and has at least two outlets to allow water to exit the enclosure. The enclosure contains a plurality of movable particles. The movable particles have dimensions selected to prevent the movable particles from passing out of the enclosure via the outlets. The apparatus further comprise a flow generator that produces a flow of water within the enclosure from the inlet to the outlets to cause the water to flow over the surface of the sensor. The flow of the water causes at least some of the movable particles to impinge on the surface of the sensor to inhibit build-up of contaminates on the surface. The outlets of the enclosure are oriented with respect to the flow of the water to inhibit the movable particles from blocking the outlets.

In certain embodiments of the apparatus, the enclosure comprises an inner cavity configured to constrain the movable particles in a volume proximate to the surface of the sensor. Preferably, the inner cavity has a shape selected to cause the movable particles to move in a circulating pattern within the inner cavity.

BRIEF DESCRIPTION OF THE DRAWINGS

Embodiments in accordance with aspects of the present invention are described below in connection with the attached drawings in which:

FIG. 6 illustrates an exploded perspective view of the sensor system of FIG. 1 viewed from the proximal end of the sensor system;

FIG. 7 illustrates an exploded perspective view of the sensor system of FIG. 1 viewed from the distal end of the sensor system;

FIG. 8 illustrates an enlarged exploded perspective view of the sensor housing of the sensor system of FIG. 1 viewed from the proximal end of the sensor housing;

FIG. 9 illustrates an enlarged exploded perspective view of the sensor housing of the sensor system of FIG. 1 viewed from the distal end of the sensor housing;

FIG. 10 illustrates a perspective view of the pH sensor of the sensor housing of FIGS. 8 and 9 viewed from the distal end of the pH sensor;

FIG. 11 illustrates a perspective view of the chlorine sensor of the sensor housing of FIGS. 8 and 9 viewed from the distal end of the chlorine sensor;

FIG. 12 illustrates a perspective view of the temperature sensor of the sensor housing of FIGS. 8 and 9 viewed from the distal end of the temperature sensor;

FIG. 13 illustrates an elevational view of the distal end of the sensor body of FIGS. 8 and 9 before adding components to the sensor body;

FIG. 14 illustrates an elevational view of the proximal end of the sensor body of FIGS. 8 and 9 before adding components to the sensor body;

FIG. 15 illustrates a cross-sectional perspective view of the sensor body of FIGS. 8 and 9 as viewed from the proximal end, the cross section taken along the line 15-15 in FIG. 14 to pass through the centers of the bores that receive the motor and the impeller;

FIG. 16 illustrates a cross-sectional perspective view of the sensor body of FIGS. 8 and 9 as viewed from the proximal end, the cross section taken along the line 16-16 in FIG. 14 to pass through the approximate center of the bore that receives the chlorine sensor;

FIG. 17 illustrates an exploded perspective view of the motor assembly and the impeller assembly of the sensor housing as viewed from the distal end of the sensor system;

FIG. 18 illustrates an exploded perspective view of the impeller assembly of FIG. 17 as viewed from the proximal end of the impeller assembly;

FIG. 19 illustrates a cross-sectional elevational view of the assembled sensor housing of FIG. 9 without the sensor cover, the cross section taken along the line 19-19 in FIG. 9 to pass through the approximate center of the sensor body;

FIG. 20 illustrates a perspective view of the cover of the sensor housing of FIGS. 8 and 9 viewed from the proximal end of the sensor cover;

FIG. 21 illustrates a perspective view of the cover of the sensor housing of FIGS. 8 and 9 viewed from the distal end of the sensor cover;

FIG. 22 illustrates an elevational view of the proximal end of cover of the sensor housing of FIGS. 8 and 9;

FIG. 23 illustrates a perspective cross-sectional view of the cover the sensor housing of FIG. 22 taken along the line 23-23 in FIG. 20;

FIG. 24 illustrates an elevational view of the distal end of the sensor housing with the housing cover illustrated in phantom to show the components within the housing cover;

FIG. 36 illustrates an exploded perspective view of the sensor housing of FIGS. 32 and 33 viewed from the proximal end of the sensor housing;

FIG. 37 illustrates an exploded perspective view of the sensor housing of FIGS. 32 and 33 viewed from the distal end of the sensor housing;

FIG. 38 illustrates a perspective view of the pH/reference probe incorporated into the sensor housing of FIGS. 32 and 33 viewed from the proximal end of the pH/reference probe;

FIG. 39 illustrates a perspective view of the pH/reference probe incorporated into the sensor housing of FIGS. 32 and 33 viewed from the distal end of the pH/reference probe.

DETAILED DESCRIPTION OF PREFERRED EMBODIMENTS

The amperometric sensor is disclosed herein with respect to exemplary embodiments. The embodiments are disclosed for illustration of the sensor system and are not limiting except as defined in the appended claims.

Figure 1:
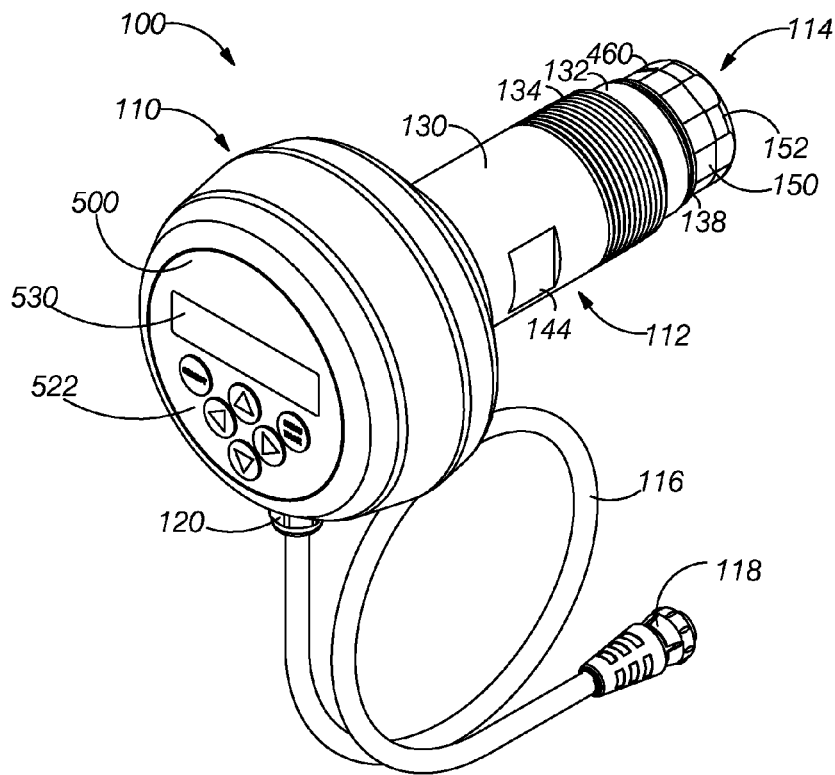
FIG. 1 illustrates a perspective view of an embodiment of a sensor system as viewed from the proximal end of the sensor system.

FIG. 1 illustrates a perspective view of an embodiment of a sensor system 100 in accordance with aspects of the present invention. The sensor system comprises an electronics enclosure 110, an intermediate housing 112, a sensor housing 114 and a communications cable 116. The communications cable is terminated at a free end with a connector 118. The opposite end of the communications cable enters the electronics enclosure via a liquid-tight cordgrip 120. Wires within the communications cable are terminated on a printed circuit board (not shown in FIG. 1) within the electronics enclosure as described below.

Figure 2:
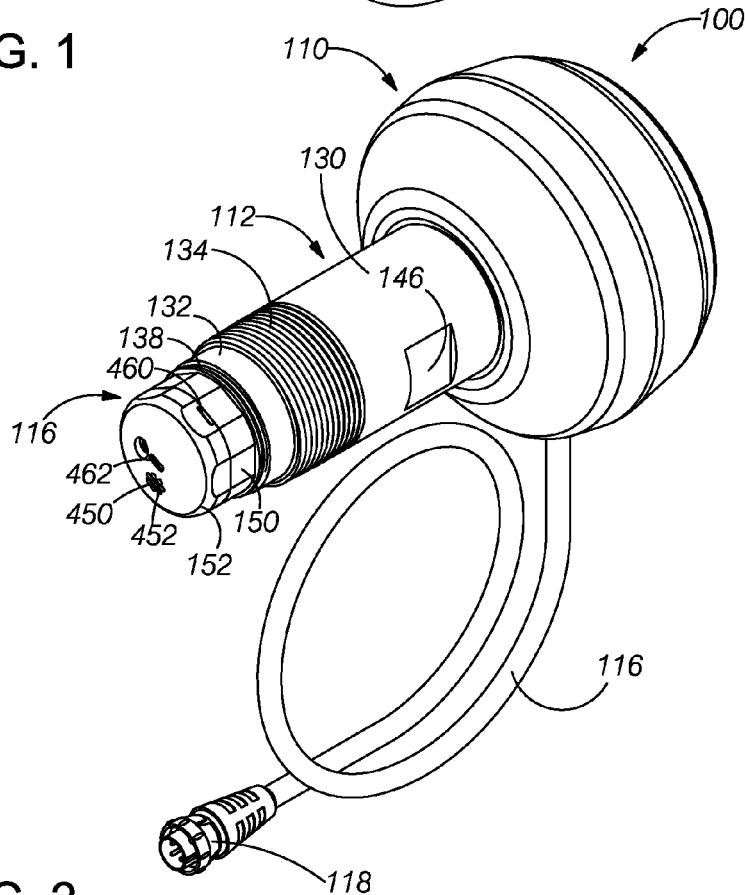
FIG. 2 illustrates a perspective view of an embodiment of the sensor system of FIG. 1 as viewed from the distal end of the sensor system.
Figure 3:
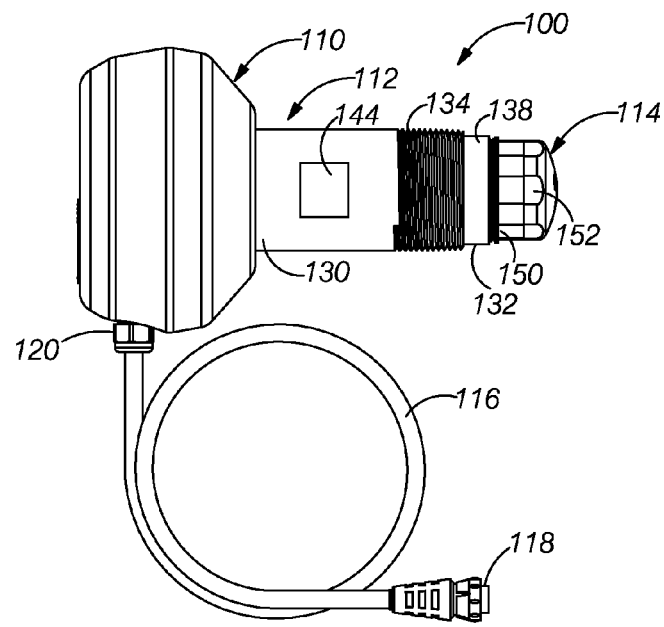
FIG. 3 illustrates a right side elevational view of the sensor system of FIG. 1.
Figure 4:
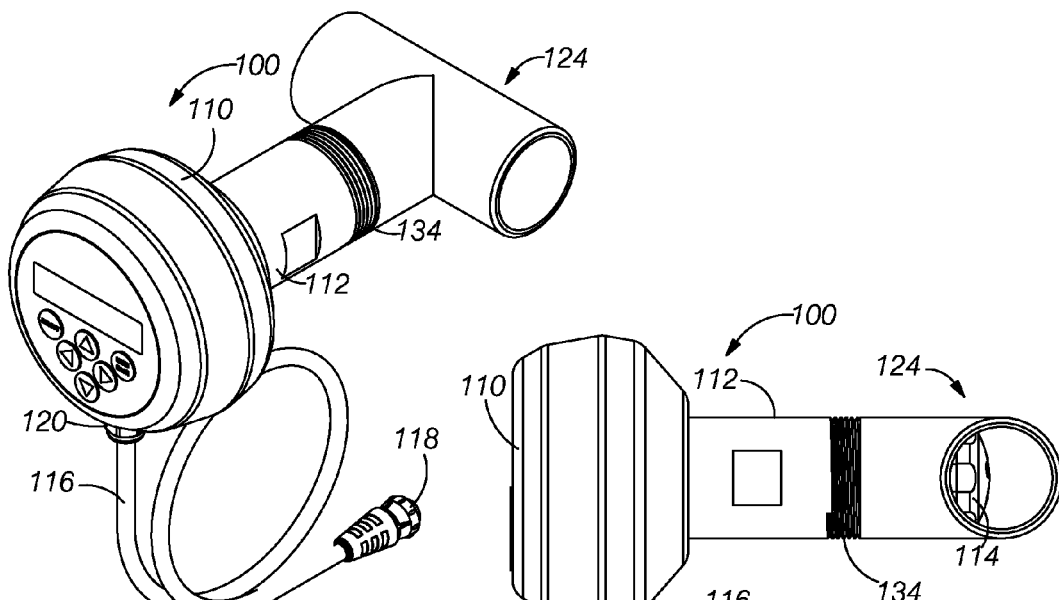
FIG. 4 illustrates a perspective view of the sensor system of FIG. 1 when engaged with a pipe fitting in a water system.
Figure 5:
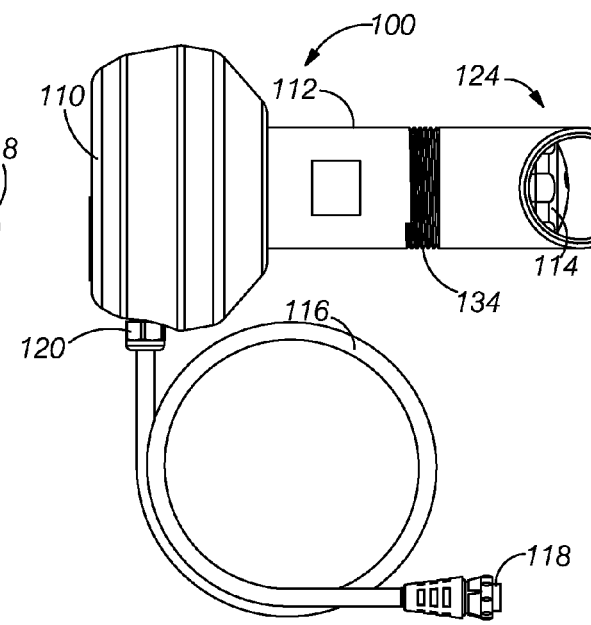
FIG. 5 illustrates a right elevational view of the sensor system and the pipe fitting of FIG. 4 showing the sensor housing of the sensor system extending into the pipe fitting.

FIG. 2 illustrates a perspective view of the sensor system 100 of FIG. 1 viewed from the sensor end. FIG. 3 illustrates a right side elevational view of the sensor system of FIG. 1. FIG. 4 illustrates a perspective view of the sensor system engaged with a tee pipe fitting 124. FIG. 5 illustrates an end elevational view of the sensor system and pipe fitting of FIG. 4 showing the sensor housing 114 within the pipe fitting in a position such that when water is flowing through the pipe fitting the sensor housing will be immersed in the water. FIG. 6 illustrates an exploded perspective view corresponding to the view in FIG. 1. FIG. 7 illustrates an exploded perspective view corresponding to the view in FIG. 2.

As used in the following description "proximal" refers to portions of the sensor system 100 and subassemblies towards the electronics enclosure 110 (e.g., towards the left in FIG. 1) and "distal" refers to portions of the sensor system and subassemblies towards the sensor housing 114 (e.g., towards the right in FIG. 1). Accordingly, in FIGS. 4 and 5, for example, the electronics enclosure at the proximal end of the sensor system is at the left in each figure and the sensor housing at the distal end of sensor system is positioned within the pipe fitting 124 at the right in each figure.

The intermediate housing 112 of the sensor system 100 generally corresponds to a cylindrical section 130 having a nominal inner diameter and a nominal outer diameter corresponding to the inner diameter and the outer diameter, respectively, of a 1½-inch pipe. The intermediate section has an overall length of approximately 4½ inches between the proximal end and the distal end. A first end portion 132 of the intermediate housing at the distal end has a reduced outer diameter for a length of approximately 0.4 inch. An outer threaded portion 134 adjacent the first end portion has male threads that correspond to the male threads of a 1½-inch pipe such that the first end portion and the outer threaded portion can be inserted into a conventional 1½-inch pipe fitting (e.g., the fitting 124 in FIGS. 4 and 5) by engaging the male threads of the intermediate housing with the female threads of the fitting.

As shown in FIG. 7, the inner surface of the first end portion 132 and the inner surface of the outer threaded portion 134 have female threads 136 formed therein that are compatible with a 1¼-inch pipe fitting. The female threads of the intermediate housing receive male threads 138 of the sensor housing 114 when the sensor housing is attached to the intermediate housing as shown in FIGS. 1-5. A second end portion 140 of the intermediate housing at the proximal end has a reduced outer diameter and is sized to fit snugly within a circular opening 142 (FIG. 7) in the distal surface of the electronics enclosure 110.

In the illustrated preferred embodiment, the intermediate housing 112 further includes a first flat portion 144 and a second flat portion 146 that are diametrically opposed from each other along the central body 130 of the intermediate housing. The two flat portions are engageable by a wrench (not shown) so that the intermediate housing can be easily rotated to engage the outer male threads of the intermediate housing with the female threads of the pipe fitting shown in FIGS. 4 and 5.

As shown in the exploded perspective view of the sensor system 100 in FIGS. 6 and 7, the intermediate housing 112 is a conduit for interconnection cables and other equipment that extend from the sensor housing 114 to the electronics enclosure 110.

As shown in the enlarged exploded perspective views of the sensor housing 114 in FIGS. 8 and 9, the sensor housing comprises a sensor body 150 and a sensor cover 152. The sensor body has a proximal surface 154 and a distal surface 156. The sensor cover is positioned over the distal surface of the sensor body.

A pH sensor unit 160 (shown in more detail in FIG. 10) extends through the sensor body 150 from the distal surface 156 of the sensor body and projects from the proximal surface 154 of the sensor body into the intermediate housing 112 when the sensor system is assembled as show in FIGS. 1-5. A pH sensor cable 162 extends from the proximal end of the pH sensor unit to a connector 164. Preferably, the pH sensor cable is a shielded cable. The connector engages a mating connector on a printed circuit board (described below) within the electronics enclosure 110. The pH sensor provides a pH signal on one wire of the pH signal cable and a common reference signal on another wire of the pH signal cable. An active distal end 166 of the pH sensor is exposed at the distal surface of the sensor body. Preferably, the pH sensor is a replaceable pH sensor, which may be a single-junction sensor or a double-junction sensor. In preferred embodiments, the pH sensor is a double-junction sensor.

A chlorine sensor 170 (shown in more detail in FIG. 11) extends through the sensor body 150 and extends from the distal surface 156 of the sensor body toward the proximal surface 154 of the sensor body. A chlorine sensor cable 172 extends from the proximal end of the chlorine sensor and passes through the intermediate housing 112. The chlorine sensor cable comprises a pair of chlorine sensor wires. A respective connector 174 at the proximal end of each of chlorine sensor wires engages a respective mating connector on the printed circuit board within the electronics enclosure 110. An active distal end 176 of the chlorine sensor is exposed at the distal surface of the sensor body. The active distal end of the chlorine sensor comprises a pair of electrodes 178. One of the electrodes is a working electrode, and the other electrode is an auxiliary electrode. A respective one of the electrodes is connected to a respective one of the chlorine sensor wires.

The chlorine sensor 170 is a long-life chlorine sensor, which may have different configurations. In one advantageous configuration, the chlorine sensor comprises a platinum working electrode and a platinum auxiliary electrode. In another advantageous configuration, the chlorine sensor comprises a platinum auxiliary electrode and a gold working electrode. The platinum electrode may comprise an alloy of platinum. The gold electrode may comprise an alloy of gold. In another configuration, both electrodes are platinum. In another configuration, both electrodes are gold. Preferably, the chlorine sensor is enclosed within a housing comprising polyether ether ketone (PEEK), a semicrystalline thermoplastic having excellent mechanical properties and chemical resistance properties. Alternatively, the platinum metal may be deposited on a non-conductive water resistant substrate (such as ceramic PCB material) by plating, vapor deposition or other means to form a concentric ring and a disk. A conductive path is formed using a selected metal, such as silver, using a printed circuit board process known as "via-in-pad, conductive silver via plug with planarized surface copper." This process developed by the Via Protection Task Group (D-33d) of the Rigid Printed Circuit Board Committee (D-30) of the IPC (IPC, 3000 Lakeside Drive, Suite 309S, Bannockburn, Ill. 60015-1219) provides a conductive pad without producing any holes in the printed circuit board, thus facilitating sealing and waterproofing.

A temperature sensor 180 (shown in more detail in FIG. 12) is embedded within the sensor body 150. A temperature sensor cable 182 extends from the proximal end of the temperature sensor and passes out from the proximal surface 154 of the sensor body and then through the intermediate housing 112. A connector 184 on the proximal end of the temperature sensor cable engages a mating connector on the printed circuit board within the electronics enclosure 110. In the illustrated embodiment, the temperature sensor cable comprises a plurality of signal wires (e.g., 4 signal wires), and the connector comprises a corresponding plurality of connector elements. In the illustrated embodiment, the temperature sensor comprises a printed circuit board 186 onto which are mounted components that generate signals responsive to the temperature of the components. Preferably, the printed circuit board is surrounded by a cylindrical plug 188 (shown in phantom) that comprises a thermally conductive potting compound. Accordingly, the temperature of the sensor body is communicated to the temperature sensor.

A motor assembly 190 is mounted on the proximal surface 154 of the sensor body 150. The motor assembly comprises a motor 192 mounted to the sensor body via a motor assembly bracket 194. A motor power cable 196 extends from the motor and through the intermediate housing 112. A connector 198 on the motor power cable engages a mating connector on the printed circuit board.

The sensor body 150 prior to assembly is shown in FIGS. 13-16. As shown in the cross-sectional view in FIG. 15, the sensor body includes a first through bore 200 that extends from the distal surface 156 to the proximal surface 154. The diameter of a first portion 202 of the first through bore proximate the distal surface is larger than the diameter of a second portion 204 of the first through bore proximate the proximal surface so that the first through bore includes a taper 206 between the two portions. The pH sensor unit 160 (FIG. 10) includes a taper 210 that rests against the taper of the sensor body when the pH sensor is inserted into the first through bore. An O-ring 212 around the pH sensor unit distal to the taper seals the first portion of the first through bore to inhibit liquid flow through the first through bore. If necessary, the pH sensor can be replaced by pushing the pH sensor out from the distal end of the sensor body and inserting a replacement pH sensor with the attached O-ring into the first through bore until the replacement pH sensor seats against the taper.

As shown in the cross-sectional view in FIG. 16, the sensor body 150 includes a second through bore 220. The second through bore has a first larger diameter portion 222 proximate the distal surface 156 and a second smaller diameter portion 224 proximate the proximal surface 154. A taper 226 interconnects the two portions. The chlorine sensor 170 (FIG. 11) includes a taper 230 that rests against the taper of the sensor body when the chlorine sensor is inserted into the second through bore. An O-ring 232 proximal to the taper on the chlorine sensor seals the second through bore to inhibit liquid flow through the second through bore. If necessary, the chlorine sensor can be replaced by pushing the chlorine sensor out from the distal end of the sensor body and inserting a replacement chlorine sensor with the attached O-ring into the second through bore until the replacement chlorine sensor seats against the taper.

As shown in the cross-sectional view in FIG. 15, the distal surface 152 of the sensor body 150 includes a first distal blind bore 240 that extends for a first selected distance into the sensor body. A secondary distal blind bore 242 at the bottom of the first distal blind bore has a smaller diameter that extends a second distance further into the sensor body. The secondary distal blind bore is concentric with respect to the first distal blind bore about a common axis 244.

As shown in the cross-sectional view in FIG. 15, the sensor body 150 further includes a first proximal blind bore 250 that has a diameter sized to receive the temperature sensor 180 (FIG. 12). As shown in FIG. 12, the temperature sensor preferably is embedded in the cylindrical thermally conductive epoxy plug 188, which has an outer diameter corresponding to the diameter of the first proximal blind bore so that the temperature sensor fits snugly within the first proximal blind bore. Accordingly, the temperature of the sensor body is communicated to the printed circuit board 186 of the temperature sensor via the plug.

The proximal surface 154 of the sensor body 150 includes a second proximal blind bore 260 having a first portion 262 with a larger diameter at the proximal surface and having a second portion 264 with a smaller diameter in the direction towards the distal surface 156. A ledge 266 is formed between the first portion and the second portion. The second proximal blind bore is concentric with respect to the common axis 244 and is thereby aligned with the first distal blind bore 240 and the secondary distal blind bore 242. A distal portion 270 of the second portion of the second proximal blind bore is annular so that a shell 272 is formed around the first distal blind bore and the second distal blind bore. As shown in FIG. 15, the shell precludes the passage of liquid from the first distal blind bore and the secondary distal blind bore to the first proximal blind bore.

The second proximal blind bore 260 of the sensor body 150 receives the components of the motor assembly 190 shown in an exploded perspective view in FIG. 17. The motor assembly includes the electrically powered motor 192. In the illustrated embodiment, the motor comprises a Nidec-17S brushless DC (BLDG) motor, which is commercially available from Nidec America, Braintree, Mass. In certain embodiments, the motor may be equipped with an integrated tachometer. The motor is attached to the motor support bracket 194 via a plurality of fasteners (e.g., 3 screws) 270. The bracket is attached to the proximal surface 154 of the sensor body (FIGS. 13-16) via a plurality of fasteners (e.g., 2 screws) 272 that engage a corresponding plurality of threaded bores 274 (FIG. 14) in the proximal surface of the sensor body. The bracket is aligned with the sensor body via a pair of alignment studs 276 that fit into a corresponding pair of alignment bores 278 (FIG. 14) in the proximal surface of sensor body. When the bracket is aligned and secured, the position of the bracket aligns the rotational axis of the motor with the common axis 244. An output shaft 280 of the motor extends into the first portion 242 of the second proximal blind bore. A coupler 282 couples the output shaft to a ring magnet 284. Preferably, the ring magnet comprises a neodymium magnet. The motor is driven by power provided by the power cable 196 (shown in FIGS. 8 and 9).

The first distal blind bore 240 receives the shaft 302 of an impeller assembly 300 shown in an exploded perspective view in FIG. 17 and also shown in FIG. 18. The impeller assembly comprises an impeller disk 304 having a plurality of curved impeller blades 306 attached to the distal face. The shaft extends from the proximal face of the impeller disk. The shaft comprises a distal shaft portion 310 having a cavity 312 (FIG. 18) and a proximal shaft portion 314 having a cavity 316. The cavities in the two shaft portions receive a rod magnet 318. The two shaft portions are then attached (e.g., with an adhesive) to secure the rod magnet therein. The two shaft portions of the impeller shaft have an outer diameter that is slightly less than the inner diameter of the first distal blind bore 240. The impeller assembly further includes a first axial bearing 320 that extends distally from the center of the impeller blades. As show in FIG. 18, the proximal shaft portion further includes a second axial bearing 322 that extends proximally from the center of the proximal shaft portion. The second axial bearing is sized to fit within the secondary distal blind bore 242. The impeller may be constructed as one seamless piece by injection molding the impeller and insert molding the magnet such that it is fully encapsulated within the impeller shaft.

As shown in the cross-sectional view in FIG. 19, when the motor assembly 190 is secured to the proximal surface 154 of the sensor body 150, the ring magnet 284 is positioned around the shell 272 formed around the first distal blind bore 240 and the secondary distal blind bore 242. When the shaft is fully inserted into the first distal blind bore, the rod magnet 314 is positioned within the magnetic field of the ring magnet 284 (e.g., the rod magnet is concentric with the ring magnet and generally laterally aligned with the ring magnet). Accordingly, when the ring magnet is rotated by the motor 192, the rod magnet rotates synchronously with the ring magnet and causes the impeller assembly 300 to rotate. Thus, the motor rotates the impeller without requiring a continuous mechanical contact that would require an opening through the sensor body 150. Accordingly, no O-rings or other seals are required to prevent fluid flow around a rotating shaft. Preferably, the motor has a known maximum torque. In the illustrated embodiment, the magnetic coupling force between the ring magnet and the rod magnet is selected to be greater than the maximum torque of the motor. Accordingly, if a locked impeller condition should occur, the torque of the motor would be insufficient to rotate the ring magnet with respect to the immobile rod magnet. Accordingly, neither the ring magnet nor the rod magnet will be demagnetized by any relative rotational movement between the two magnets.

It can be seen that the respective distal surfaces of the sensor body 150 and the sensor housing 114 comprise a "wet side" of the sensor housing. The proximal surfaces of the sensor body and the sensor housing are isolated from any water on the wet side and thereby comprise a "dry side" of the sensor housing. The motor 192 is mounted on the dry side of the sensor housing. The impeller assembly 300 is mounted on the wet side of the sensor housing. The shell 272 surrounding the impeller shaft 302 isolates the wet side and the dry side. The ring magnet 284 and the rod magnet 318 provide magnetic coupling through the shell such that rotation of the motor on the dry side of the housing rotates the impeller on the wet side of the housing.

As shown above in FIGS. 8 and 9, for example, the distal surface 156 of the sensor body 150 of the sensor housing 114 is covered by the sensor cover 152. The sensor cover is configured to direct the flow of fluids over the exposed distal end 166 of the pH sensor 160 and the exposed distal end 176 of the chlorine sensor 170. As shown in more detail in FIGS. 20-24, the sensor cover has a proximal surface 400 and a distal surface 402. A plurality of protrusions 410 (e.g., 3 protrusions) extend from the proximal surface of the sensor cover and engage a corresponding plurality of recesses 412 (FIG. 9) in the distal surface of the sensor body 150 to align the sensor cover with the sensor body. A countersunk bore 414 extends from the distal surface to the proximal surface of the sensor cover. As shown in FIG. 9, the countersunk bore receives a fastener (e.g., a screw) 416 that engages a blind bore 418 in the distal surface of the sensor body (see FIG. 13) to secure the sensor cover to the sensor body.

The proximal surface of the sensor cover 152 has a recessed fluid channel 430 formed therein. The recessed fluid channel has a first generally cylindrical portion 432, a second tapered portion 424 and a third generally oval-shaped (ovoidal) portion 436. The first fluid channel portion is configured to receive the disk 304 and the blades 306 of the impeller assembly 300 so that the disk and impeller blades are able to rotate freely within the first portion. The relationship between the impeller and the first fluid channel portion is shown in the distal view in FIG. 24 wherein the sensor cover is shown as transparent and the fluid channel is shown in phantom lines. A first bore 450 extends distally from the first portion and is positioned and sized to receive the axial extension 320 of the impeller assembly (shown in FIG. 17). The first bore of the sensor cover functions as a distal bearing for the impeller. A plurality of through bores 452 (e.g., 6 through bores) are disposed about the first bore and provide fluid access from the distal surface of the sensor cover into the first portion of the fluid channel.

The first portion 432 of the fluid channel 430 is coupled directly to the wider entry to the tapered second portion 434 of the fluid channel. The second portion of the fluid channel tapers to a narrower cross section at the entry to the third portion 436.

As shown in FIG. 24, the third portion 436 of the fluid channel 430 is positioned to generally surround the distal end 166 of the pH sensor 160 and the distal end 176 of the chlorine sensor 170. The fluid entering the third portion exits via a radial outlet channel 460 formed on the proximal surface of the sensor cover 152. The position of the radial outlet channel is advantageous because when the sensor system 100 is inserted horizontally into a pipe fitting, as shown for example in FIGS. 4 and 5, the radial outlet channel is oriented upwardly as shown so that captured air can be purged during operation.

The fluid within the third portion 436 of the fluid channel 430 also exits via an L-shaped outlet channel 462, which has an entry across from the radial outlet channel 460. As shown in the cross-sectional view in FIG. 23, the L-shaped channel exits radially inwardly from the third portion of the fluid channel and then turns to exit perpendicularly outwardly from the distal surface 402 of the sensor cover.

When the impeller assembly 300 is caused to rotate by the motor 192, fluid from the fluid system being measured is drawn into the first portion 432 of the fluid channel 430 via the plurality of through bores 452 and is impelled outward by the impeller blades 306. The fluid exits the first portion via the tapering second portion 434 and enters the oval-shaped third portion 436. The fluid flows throughout the third portion and then exits via the two outlet channels 460, 462 to return to the fluid system being measured. Accordingly, the distal end 166 of the pH sensor 160 and the distal end 176 of the chlorine sensor 170 are continually refreshed with fluid from the fluid system being measured.

As further shown in FIGS. 9 and 24, for example, the third portion 436 of the fluid channel 430 has a plurality of movable objects (or particles) 470 positioned therein. For example, in the illustrated embodiment, the movable objects are spherical and are referred to herein as balls. It should be understood that the movable objects may have other shapes. In the illustrated embodiment, the balls move throughout the third portion in response to the fluid created by the impeller assembly 300 in the first portion 432 of the fluid channel. In the illustrated embodiment, the balls advantageously comprise polytetrafluoroethylene (PTFE) (e.g., Teflon® resin) balls, glass balls or balls of other suitable material. In some cases, it is preferable to use PEEK balls in a seawater oxidant sensor. For example, in one embodiment, the balls have diameters of approximately 0.125 inch. The movement of the balls in response to the moving fluid simultaneously cleans scale and other contaminants from both the distal end 166 of the pH sensor 160 and from the distal end the electrodes at the distal end 176 of the chlorine sensor 170.

The dimensions of the movable objects 470 (e.g., the diameters of the balls in the illustrated embodiment) are sufficiently large with respect to the second portion 434 and with respect to the outlet channels 460, 462, that the movable objects (e.g., the balls) are prevented entering the narrow end of the second portion 434 of the fluid channel and from exiting via either of the outlet channels. As shown in FIG. 23, for example, the third portion of the fluid channel is deeper proximate to the inlet from the second portion of the fluid channel to cause the balls to return to the vicinity of the inlet and be recirculated within the generally oval-shaped third portion 436 of the fluid channel over the distal ends of the pH sensor and the chlorine sensor. In an alternative embodiment (not shown), the third portion of the fluid channel may be configured so that the balls are constrained to circulate only in the vicinity of the pH sensor so that only the pH sensor is affected by the cleaning action of the balls.

Figure 25:
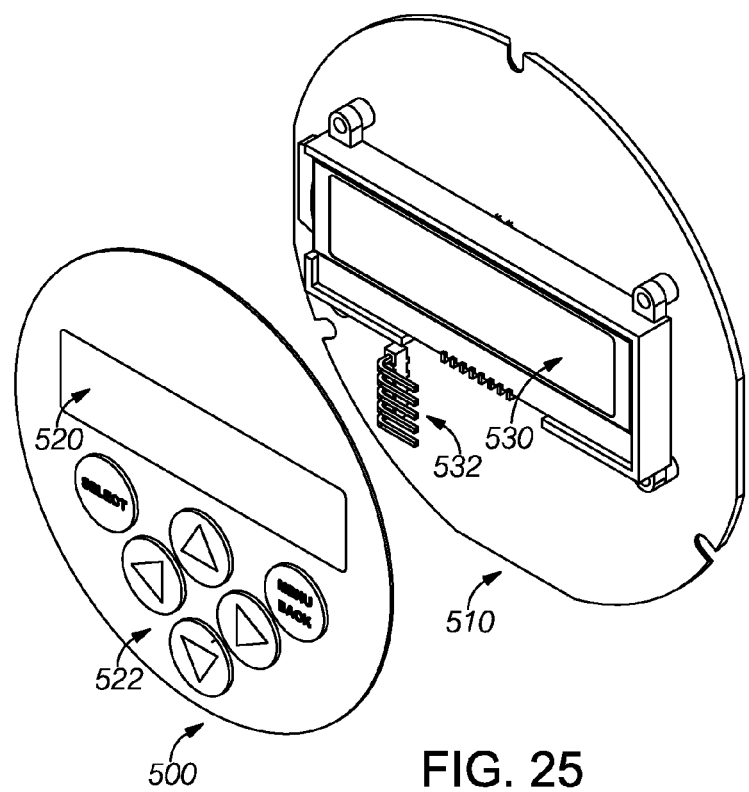
FIG. 25 illustrates an exploded perspective view of the panel and printed circuit board of the electronics enclosure of the sensor system of FIG. 1 viewed from the proximal surface of the panel.
Figure 26:
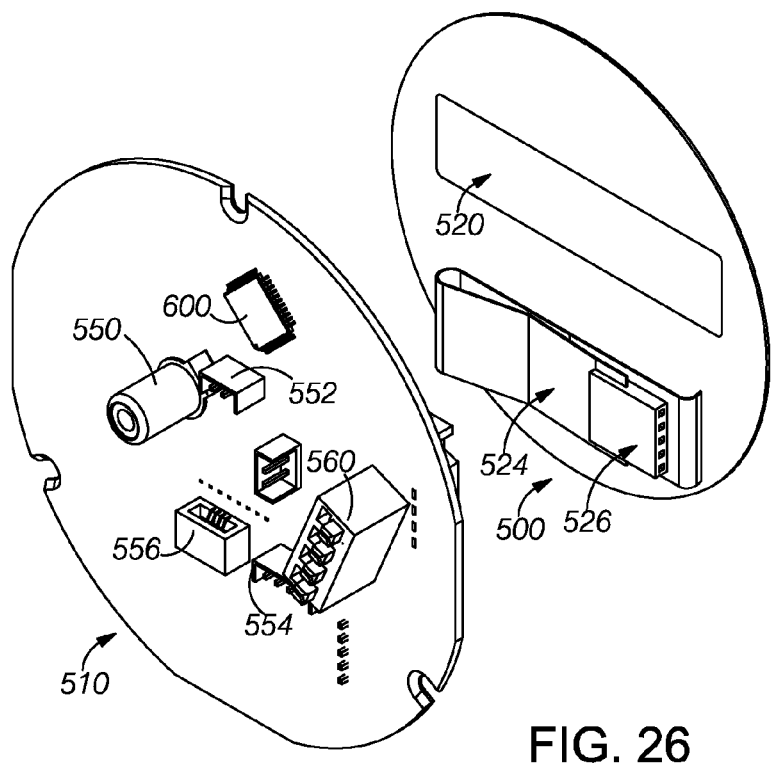
FIG. 26 illustrates an exploded perspective view of the panel and circuit board of the electronics enclosure of the sensor system of FIG. 1 viewed from the distal surface of the printed circuit board.

FIG. 25 illustrates an exploded perspective view of the respective proximal surfaces of a display and switch panel 500 and a printed circuit board 510 within the electronics enclosure 110. FIG. 26 illustrates an exploded perspective view of the respective distal surfaces of the display and switch panel and the printed circuit board. The proximal surface of the display and switch panel includes a display window 520 and a set 522 of membrane switches (described below). The distal surface of the display and switch panel includes a flexible cable 524 connected to the set of membrane switches terminated in a connector 526. The proximal surface of the printed circuit board supports an liquid crystal display (LCD) 530, which is aligned with the display window of the display and switch panel. The proximal surface of the printed circuit board further includes a connector 532 that engages the connector from the display and switch panel to electrically connect the set of membrane switches to the printed circuit board.

The distal surface of the printed circuit board 510 includes a first connector 550 that engages the connector 164 on the pH sensor cable 162. A second connector 552 engages the two connectors 174 on the chlorine sensor cable 172. A third connector 554 receives the connectors 184 on the temperature sensor cable 182. A fourth connector 556 engages the connector 198 on the motor power cable 196. A fifth connector 560 engages a connector on the cable 116 (FIGS. 1-5). For example, in one embodiment the fifth connector comprises two contacts for power and ground and two contacts the data communications signals.

A processor 600 on the distal surface of the printed circuit board 510 controls the motor 192 by providing signals to the motor via the motor power cable 196. The processor receives the signals from the pH sensor 160, the chlorine sensor 170 and the temperature sensor 180 and provides the signals as formatted output signals via the cable 116. For example, the output signals may be provided via a standard two-wire RS-232 current loop via the connector 560. The processor further controls the information displayed on the LCD 530. The processor is responsive to signals received from the set 522 of membrane switches on the display and switch panel 500. For example, the processor advantageously displays a user menu on the LCD, and a user is able to scroll through the menu using a scroll up switch, a scroll down switch, a scroll left switch and a scroll right switch. The user is able to select menu options and enter values using the scroll switches and a select switch. The user is able to return to previous menu options with a menu back switch.

In an alternative embodiment wherein the control of the sensor system 100 and the monitoring of the measurements are done entirely by a remote system via the cable 116, the LCD panel and the membrane switches may be omitted. In such an embodiment, the proximal surface of the electronics enclosure 110 is covered with a blank panel (not shown).

Figure 27:
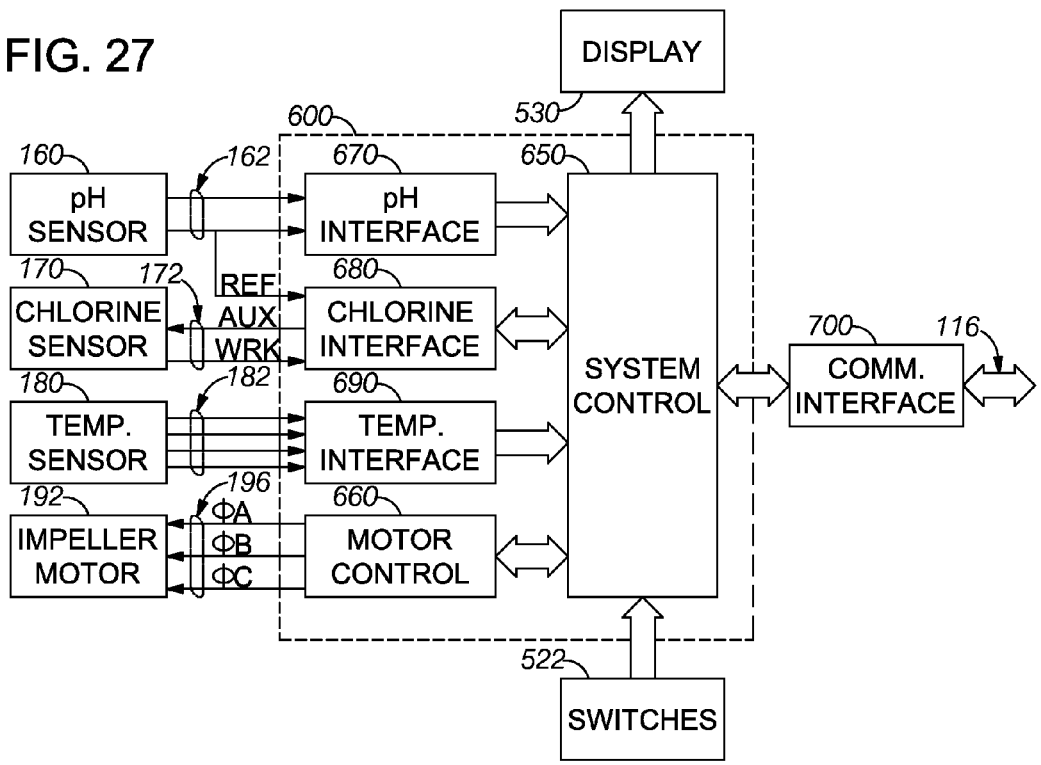
FIG. 27 illustrates a block diagram of the electronics system of the sensor system of FIG. 1.

FIG. 27 illustrates a simplified block diagram of the electrical circuitry of the system 100. The set 522 of the membrane switches and the LCD 530 are connected to the processor 600 as described above. The processor includes a system controller 650, which is advantageously a programmable processor that communicates with other devices via conventional input/output ports.

The system controller 650 is coupled to a motor controller 660, which generates three motor phase signals φA, φB and φC and provides the signals to the motor 192 via the motor control cable 196 in a selected sequence to control the rotation of the motor.

The system controller 650 is coupled to a pH sensor interface 670 that monitors the pH sensor 160 via the cable 162. For example, the pH sensor interface advantageously includes an analog-to-digital converter to convert the measured voltages from the pH sensor into a digital representation of the measured voltages.

The system controller 650 is coupled to a chlorine sensor interface 680 that applies voltages to the chlorine sensor 170 on an auxiliary (AUX) electrode wire in the chlorine sensor cable 172 and receives a measurable current from the chlorine sensor via a working (WRK) electrode wire in the chlorine sensor cable. The chlorine sensor interface shares a reference (REF) electrode wire with the pH sensor interface 670 via the pH sensor cable 162. The operation of the chlorine sensor to apply a voltage to the auxiliary electrode while monitoring the reference voltage and measuring the resulting current on the working electrode is well known to a person skilled in the art.

The system controller 650 is coupled to a temperature interface 690 that monitors the temperature readings on the temperature sensor 180 via the temperature sensor wires 182.

The system controller 650 is coupled to a communications interface 700. The communications interface sends and receives signals via the cable 116 and the connector 118 (FIGS. 1-5). In one embodiment, the communications interface is configured as a conventional RS-232 interface. In another embodiment, the communications interface is configured as a conventional USB interface.

Figure 28:
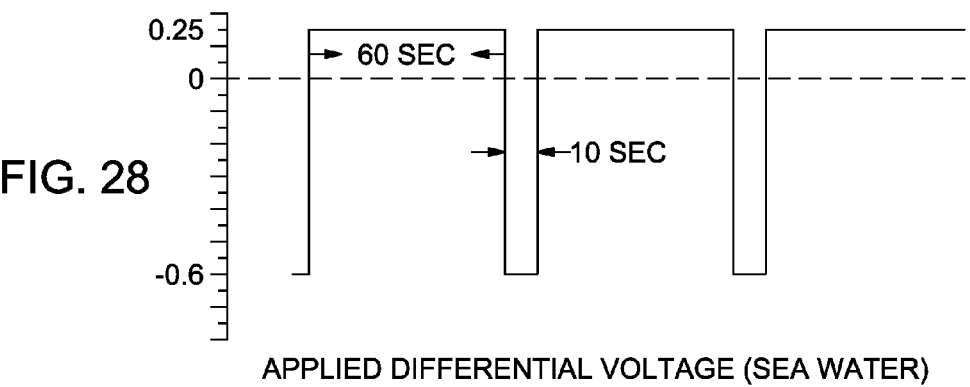
FIG. 28 illustrates a timing diagram for the differential voltage applied to the chlorine sensor when the sensor system of FIG. 1 is used to measure sea water or to measure the water in a chlorinated swimming pool.

In the illustrated embodiment, the processor operates the chlorine sensor interface 680 synchronously with the motor controller 650 to maintain the chlorine sensor electrodes in operational condition for an extended period. For example, as illustrated by a first timing diagram in FIG. 28, when the sensor system 100 is configured to measure seawater or to measure the water in chlorinated swimming pools, the differential voltage applied between the working electrode and the reference electrode starts at +0.25 volt at the beginning of the measurement cycle. The differential voltage remains at +0.25 volt for approximately 60 seconds. During the last 2 seconds of this 60-second measurement interval, the current is measured and averaged. The differential voltage is then reversed and the magnitude of the differential voltage is increased so that the differential voltage is approximately −0.6 volt. This differential voltage is maintained at approximately −0.6 volt for approximately 10 seconds to stabilize the electrodes. The measurement cycle is then repeated. During the measurement cycles, the motor controller operates the motor 192 to provide a consistent flow of water across the measurement electrodes and to move the balls 470 across the surfaces of the electrodes to prevent the build-up of scale and other materials.

Figure 29:
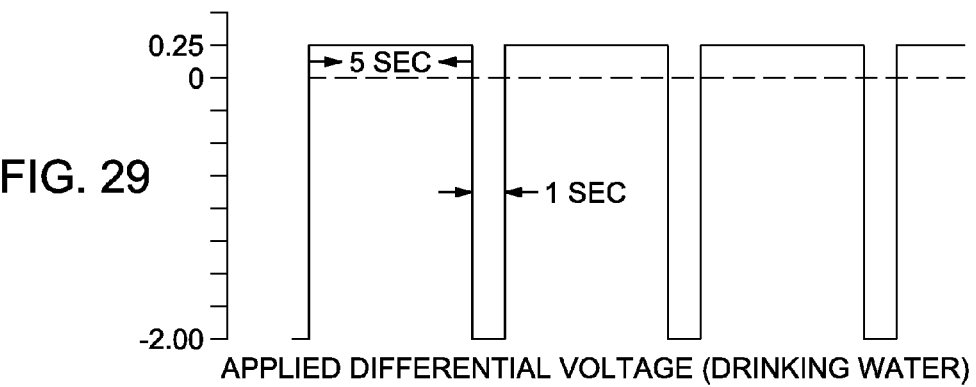
FIG. 29 illustrates a timing diagram for the differential voltage applied to the chlorine sensor when the sensor system of FIG. 1 is used to measure drinking water.

FIG. 29 illustrates a corresponding timing diagram for measuring drinking water. As in the measurement cycle for seawater and chlorinated swimming pool water, the measurement cycle for drinking water starts with the differential voltage of +0.25 volt at the beginning of the measurement cycle. The differential voltage is held at +0.25 volt for only approximately 5 seconds. The current is averaged over the last 2 seconds of this 5-second interval. The differential voltage is then lowered and the magnitude of the differential voltage is increased so that the differential voltage is approximately −2.0 volts. The differential voltage is maintained at approximately −2.0 volts for approximately 1 second to stabilize the electrodes. The measurement cycle is then repeated. Several subsequent measurements may be averaged to "smooth" out noise in the measured values. This feature may be enabled or disabled from the software interface. During the measurement cycles, the motor controller 650 operates the motor 192 as described above to cause the balls 470 to clean the surfaces of the electrodes.

The amperometric system described above in connection with the accompanying drawings has low maintenance requirements. The system is able to operate for extended periods unattended. The system operates for extended periods (e.g., for up to a year) without a sensor replacement or other maintenance. The chlorine sensor and the pH sensor are replaceable individually to reduce the cost of operation. The sensor operates in accordance with the describe method to overcome the polarization effects of cyanuric acid (CYA). The sensor does not require extensive recalibration, and if a sensor is removed or replaced, the sensor quickly stabilizes and reports reliable readings.

FIGS. 30-39 illustrate a further embodiment of a system 800. In particular. In FIGS. 30-39, elements corresponding to previously described elements are identified with corresponding element numbers.

Figure 30:
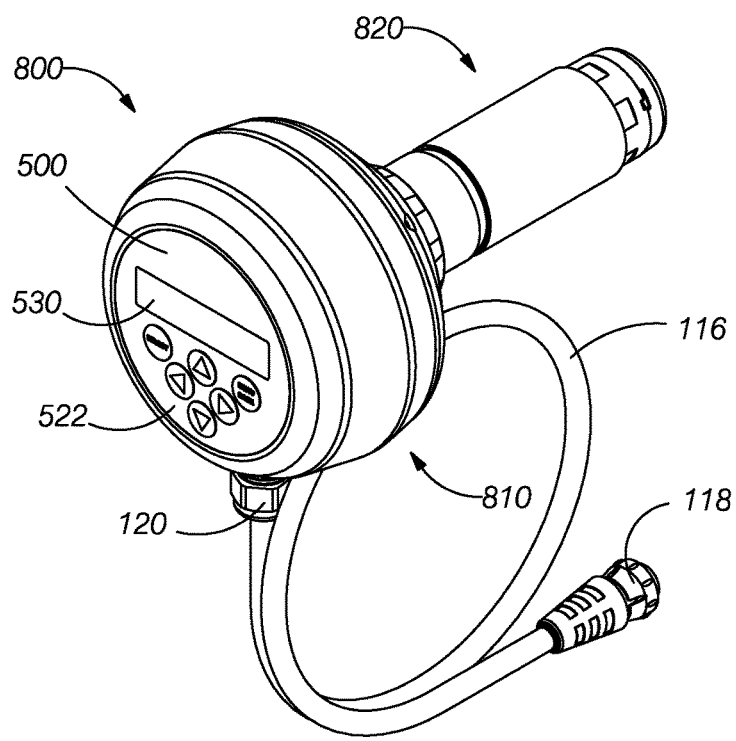
FIG. 30 illustrates a perspective view of a further embodiment of a sensor system as viewed from the proximal end of the sensor system.
Figure 31:
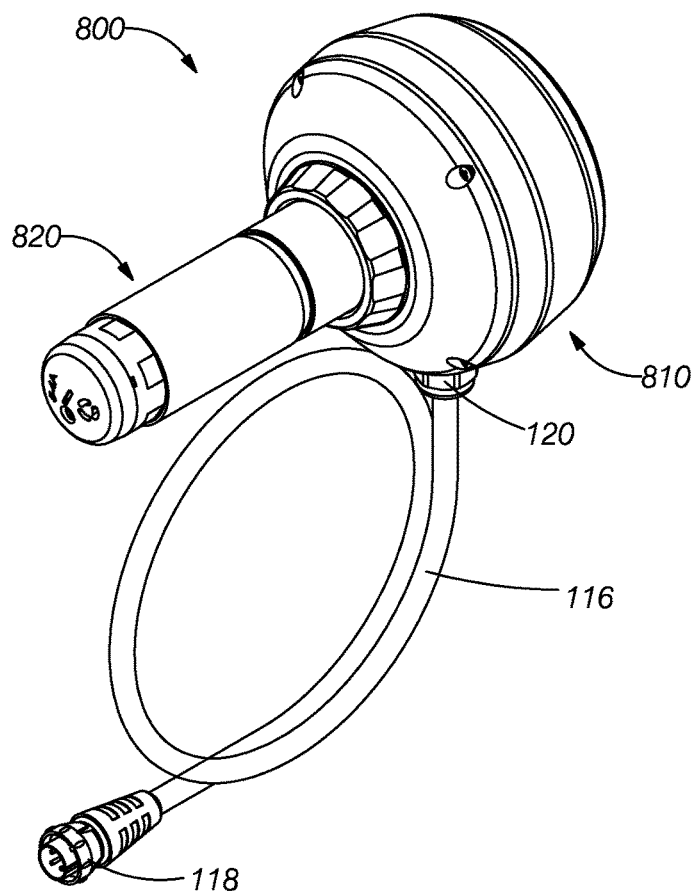
FIG. 31 illustrates a perspective view of the sensor system of FIG. 30 as viewed from the distal end of the sensor system.
Figure 32:
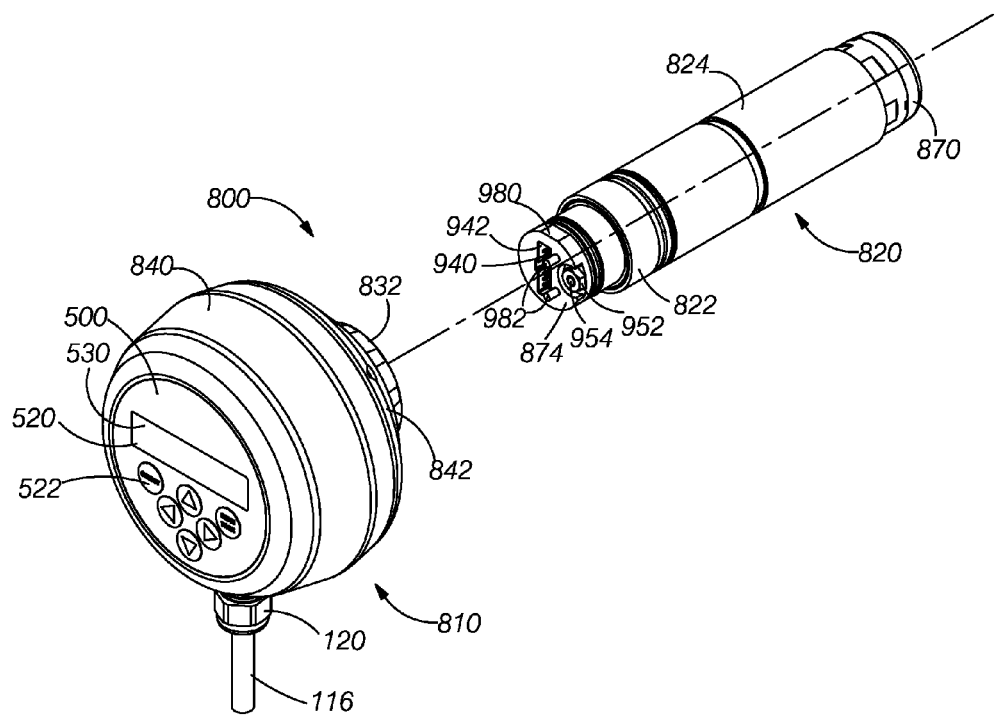
FIG. 32 illustrates an exploded perspective view of the sensor system of FIG. 30 viewed from the proximal end of the sensor system.
Figure 33:
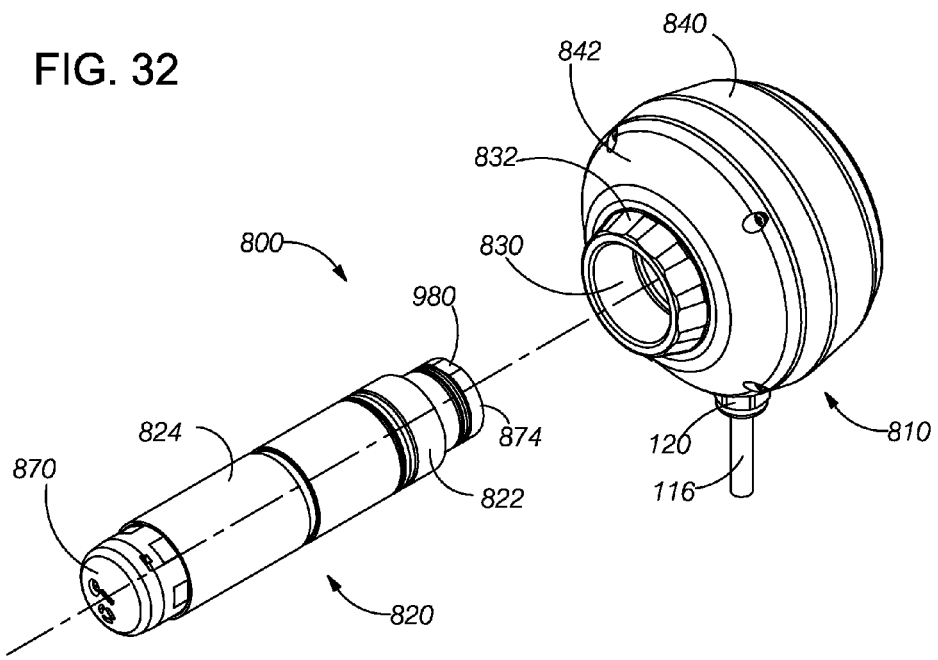
FIG. 33 illustrates an exploded perspective view of the sensor system of FIG. 30 viewed from the distal end of the sensor system.

FIG. 30 illustrates a perspective view of the sensor system 800 as viewed from the proximal end of the sensor system. FIG. 31 illustrates a perspective view of the sensor system of FIG. 30 as viewed from the distal end of the sensor system. FIG. 32 illustrates an exploded perspective view of the sensor system of FIG. 30 viewed from the proximal end of the sensor housing. FIG. 33 illustrates an exploded perspective view of the sensor system of FIG. 30 viewed from the distal end of the sensor system. The sensor system includes an electronics housing 810 at the proximal end and a sensor housing 820 at the distal end. As illustrated in the exploded views, a cylindrical proximal portion 822 of a cylindrical central housing portion 824 of the sensor housing is inserted into a distal opening 830 in the electronics housing and secured therein by a threaded collar 832. As described below in connection with FIGS. 36 and 37, a plurality of O-rings seal the cylindrical proximal portion so that water cannot enter the electronics housing via the distal opening therein.

Figure 34:
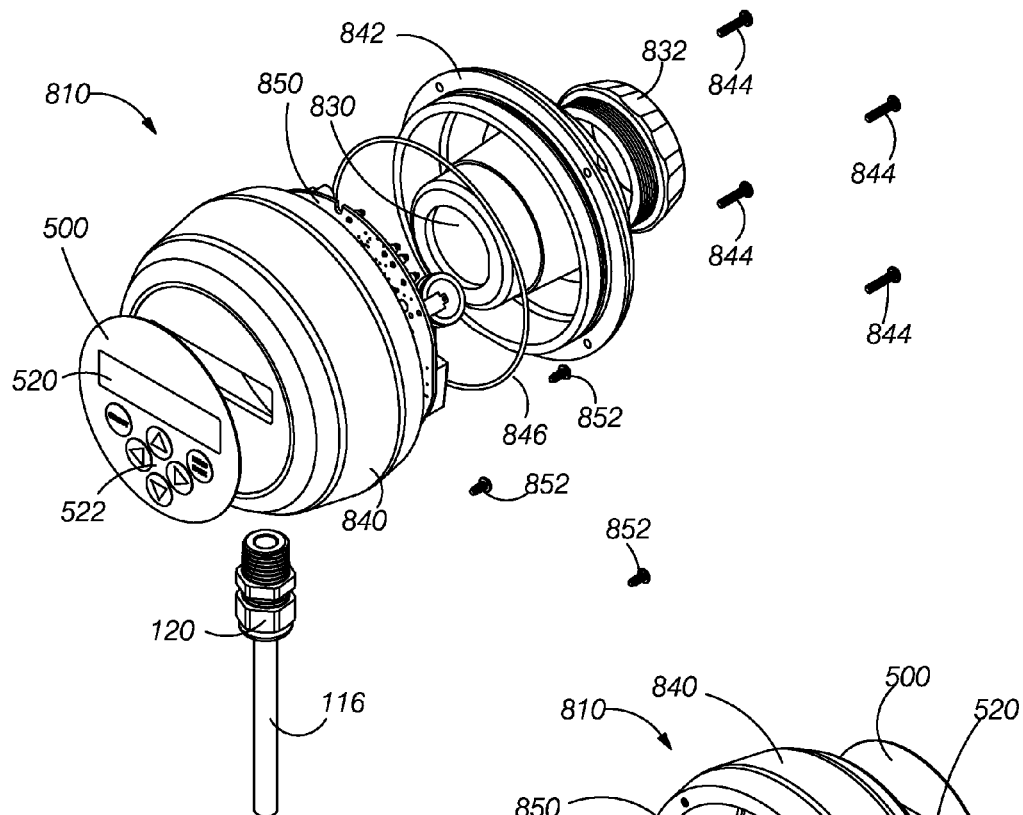
FIG. 34 illustrates an exploded perspective view of the electronics housing of FIGS. 32 and 33 viewed from the proximal end of the electronics housing.
Figure 35:
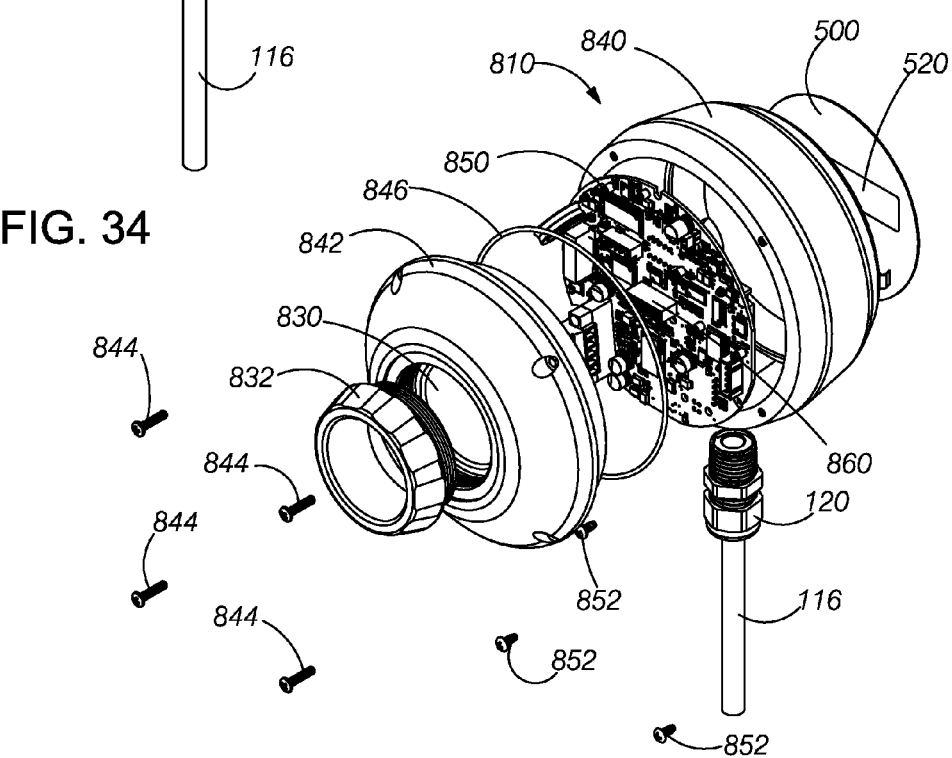
FIG. 35 illustrates an exploded perspective view of the electronics housing of FIGS. 32 and 33 viewed from the distal end of the electronics housing
Figure 40:
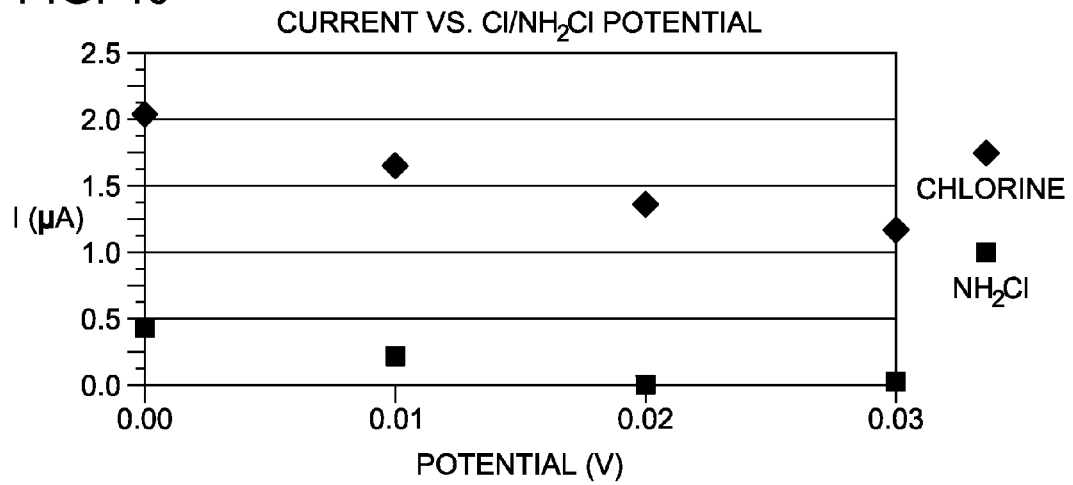
FIG. 40 illustrates a graph of sensor current (I) in microamperes versus applied potential (V) for chorine and for $NH_2Cl$.

FIG. 34 illustrates an exploded view of the electronics housing 810 of FIGS. 30-33 as viewed from the proximal end, and FIG. 35 illustrates an exploded view of the electronics housing as viewed from the distal end. The electronics housing comprises a proximal end portion 840 and a distal end portion 842 that are secured together by a plurality of screws 844. An O-ring 846 is interposed between the two portions of the electronics housing to seal the two portions when the screws are engaged. An electronics system printed circuit board (PCB) 850 is secured to the proximal end portion by a plurality of screws 852 prior to engagement of the two portions of the housing. The proximal side of the electronics system PCB includes the display and switch panel 500, which includes the set 522 of membrane switches and a display window 520. The display 530 (shown in FIGS. 30 and 32) on the electronics PCB is aligned with the display window as described above. The electronics system PCB further includes connections (not shown) to the set of membrane switches. The distal side of the electronics system PCB includes a plurality of components and connectors. In particular, a connector 860 is provided to connect with the sensor housing 820, as described below.

FIG. 36 illustrates a perspective exploded view of the sensor housing 820 viewed from the proximal end. FIG. 37 illustrates a perspective view of the sensor housing viewed from the distal end. The distal end of the sensor housing supports a sensor body 870, which is similar to the sensor body 150 described above. The cylindrical central housing portion 824 of the sensor housing extends from the sensor body to a proximal sensor end cap 874 which is mounted to the proximal end portion of the cylindrical central housing.

Unlike the previously described sensor body 150, the sensor body 870 in FIGS. 36 and 37 supports a modified pH/reference probe 880, which is shown in more detail in FIGS. 38 and 39. In particular, as shown in FIG. 39, an electrode support portion 882 at the distal end of the ph/reference probe comprises a cylindrical inner electrode 884 surrounded by a concentric annular outer electrode 886. The inner electrode is formed as a glass bulb having a flat exposed end and having an internal electrical connection. The inner electrode and the outer electrode are spaced apart by a selected distance (e.g., approximately 0.03 inch). A conventional pelon strip 888 is positioned between portions of the two electrodes. The electrical connection within the inner electrode is the measurement electrode. The outer electrode is the reference electrode. An electrical connection to the inner electrode extends to a center contact 892 of a plug 890 to provide a connection to the measurement electrode. An electrical connection to the outer electrode extends to an outer shell 894 of the plug. In the illustrated embodiment, the plug is a conventional RCA phono plug. The ph/reference probe has a hard cylindrical outer shell 896 that maintains the plug in a fixed relationship to the inner and outer electrodes.

As further illustrated in FIGS. 34 and 35, the sensor housing 820 supports a sensor housing printed circuit board (PCB) 900. The sensor housing PCB has a proximal face 902 (FIG. 37) and a distal face 904 (FIG. 36). The distal face supports a first connector 910 that is configured as a mating jack to the plug 890 so that the plug is engageable with the jack. The distal face also supports a connector 912 that receives a pair of contacts 914 on a pair of lines 916 (FIG. 36) from a chlorine sensor (not shown) that corresponds to the chlorine sensor 176 in the previously described embodiment. The distal face also supports a connector 920 that receives a connector 922 on a set of wires 924 to an impeller motor assembly 926 that corresponds to the impeller motor assembly 190 described above. The distal face also supports a connector 930 that receives a set of temperature sensor wires 932 (FIG. 37).

The proximal face 902 of the sensor housing PCB 900 supports a connector 940 that is electrically connected to the four connectors 910, 912, 920, 930 on the distal face of the PCB. The connector on the proximal face of the printed circuit board extends through an opening 942 of the proximal end cap 874 that is secured to the proximal end of the cylindrical central housing 824 of the sensor housing. The end cap is secured to the proximal end of the cylindrical portion by a washer 950 and a hex nut 952. The hex nut is threaded onto a rod 954 that extends from the sensor body 870 through a bore 956 in the end cap. When the hex nut is tightened, the sensor housing forms a rigid structure from the distal end to the proximal end, thus preventing stresses on the glass inner electrode 884 of the ph/reference sensor 880. An O-ring 960 in a groove 962 on the sensor body provides a watertight seal with respect to the surrounding cylindrical central housing.

When the proximal end 822 of the cylindrical portion 824 of the sensor housing 820 is inserted into the distal opening 830 of the electronics housing 810, the connector 930 on the proximal surface 904 of the sensor housing PCB 900 engages the connector 860 on the electronics system PCB 850 within the electronics housing. The end cap 874 includes a flat 980 that is aligned with a corresponding flat (not shown) within the distal opening of the electronics housing in order to fully insert the end cap into the distal opening. The alignment of the two flats assures that the connector on the proximal face of the circuit board within the sensor housing is properly aligned with the mating connector within the electronics housing. In addition a pair of pegs 982 fit into a pair of holes 984 in the end cap and fit into a corresponding pair of holes (not shown) in the electronics system PCB to provide additional assurance of alignment of the two connectors. All of the electrical interconnections between the sensor body 830 and the electronics PCB are completed with one connector engagement step. After engaging the connectors, the threaded collar 832 is engaged with the threads within the distal opening of the electronics enclosure to provide a mechanically secure and watertight connection between the sensor housing and the electronics enclosure. An O-ring 990 in a first groove 992 on the proximal end engages the inner surface of the distal opening of the electronics enclosure, and an O-ring 994 in a second groove 996 engages the inner surface of the threaded collar to complete the watertight seal.

As described above, the sensor system 800 is modular such that the sensor housing 820 can be easily removed from the electronics housing 810 and replaced with a sensor housing having components configured for a different application, Although described herein with respect to a sensor for a pool or a spa, it should be understood that the sensor 800 can be advantageously used to measure chlorine levels in other applications. For example, the sensor can be used to analyze the chlorine levels in the ballast tank of a ship so that when the ballast is pumped overboard as the ship is filled with cargo, the chlorine levels are within an environmentally acceptable range. As another example, the sensor disclosed herein can be used to monitor chlorine levels in drinking water.

While the description describes a sensor used for chlorine measurement, it may also be used for the measurement of bromine or TRO (total residual oxidant-chlorinated seawater that may contain bromine or both chlorine and bromine). With minor changes this sensor of the instant invention may be modified to measure peracetic acid, hydrogen peroxide and dissolved oxygen as well.

Figure 41:
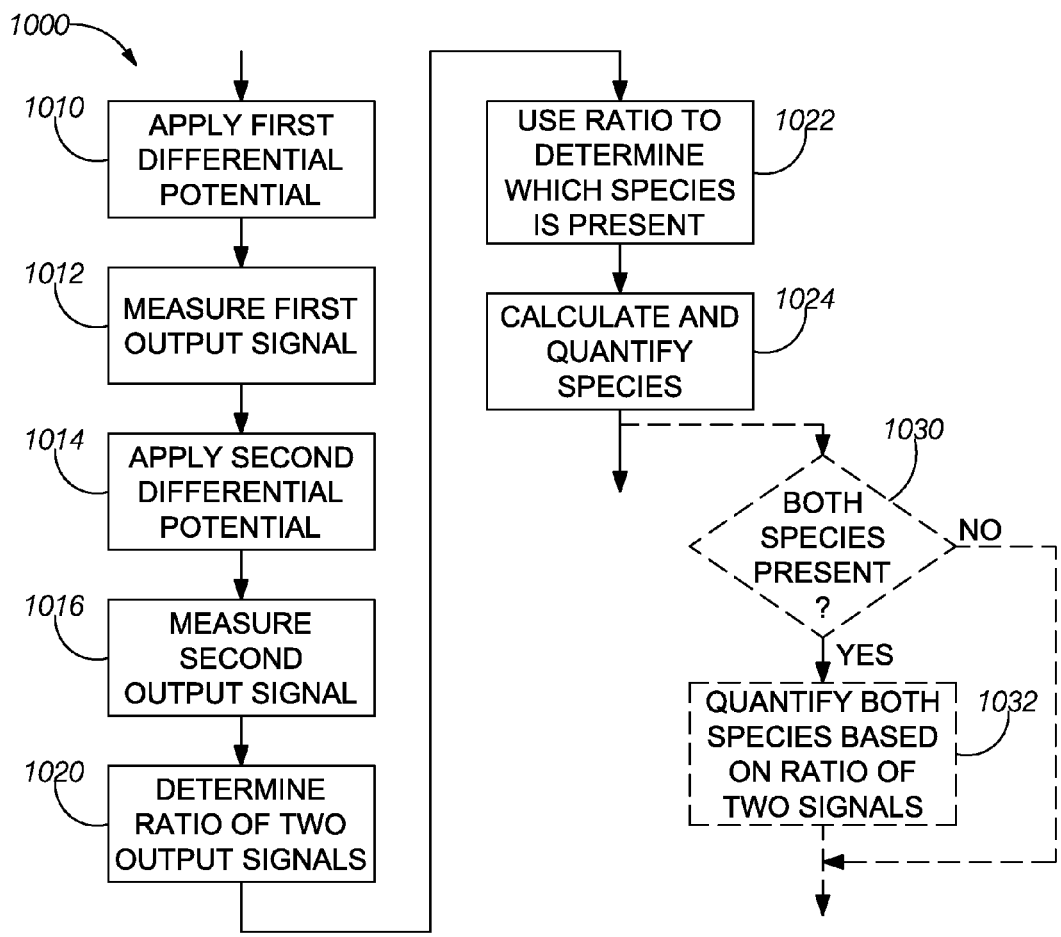
FIG. 41 illustrates a flow chart of a method of quantifying two species in water implemented by the sensor system.

The sensor system disclosed herein may be used to implement a method for quantifying two species in water as illustrated by a flow chart 1000 in FIG. 41. In an action block 1010, the system applies a first differential measurement potential between at least first and second electrodes of at least one sensor probe. Then, in an action block 1012, the system measures a first output signal responsive to the concentration of a parameter of water to be measured and responsive to the first differential measurement potential. The system then applies a second differential measurement potential between the at least first and second electrodes of the at least one sensor probe in an action block 1014. The second differential measurement potential is different from the first differential measurement potential. In an action block 1016, the system measures a second output signal responsive to the concentration of the parameter of water to be measured and responsive to the second differential measurement potential. In an action block 2020, the system determines a ratio of the first output signal to the second output signal. In an action block 1022, the system determines which of the two species is present based on the ratio of the first output signal to the second output signal. In action block 1024, the system calculates and quantifies the species determined to be present.

In an optional embodiment (illustrated by dashed lines in FIG. 41), the system determines whether both species are present in a decision block 1030. If both species are present, then, in an action block 1032, the system quantifies each species according to the ratio of the first output signal to the second output signal. If both species are not present, the system concludes the method without executing the action block 1032. In certain aspects of the method, the first species comprises free chlorine and the second species comprises chloramine; and the ratio of the first output signal to the second output signal has a value in a first range when the species in the water comprises free chlorine and has a value in a second range when the species in the water comprises chloramine.

The instant invention is capable of the measurement of up 500 ppm of TRO in seawater over repeated experimental runs, without suffering a loss of sensitivity.

As various changes could be made in the above constructions without departing from the scope of the invention, it is intended that all the matter contained in the above description or shown in the accompanying drawings shall be interpreted as illustrative and not in a limiting sense.

What is claimed is:

1. A method of operating an amperometric sensor having a plurality of electrodes positioned on the face of a sensor body, each of the plurality of electrodes having a surface exposed to water having at least one parameter to be measured by the plurality of electrodes, the method comprising:

positioning the surfaces of the plurality of electrodes in a cavity that comprises a volume of water;

providing a flow generator, the flow generator comprising an impeller and comprising a motor to impart rotation to the impeller, wherein the motor has a motor torque;

positioning the impeller in the cavity to expose the impeller to the water in the cavity;

positioning the motor outside the cavity in a location isolated from the water, the motor mechanically coupled to a first rotatable coupling device outside the cavity;

magnetically coupling the first rotatable coupling device to the impeller within the cavity to cause the impeller to rotate within the cavity, wherein the first rotatable coupling device is coupled to the impeller with at least a minimum coupling force, the minimum coupling force selected to be greater than a force provided by a maximum motor torque of the motor so that the motor will not rotate the first coupling device if the impeller cannot rotate;

operating the flow generator by applying energy to the motor to rotate the first rotatable coupling device and cause the impeller to rotate within the cavity to flow the water having the at least one parameter to be measured into, through and out of the cavity to cause the water to flow across the surfaces of the plurality of electrodes at a substantially constant velocity; and measuring the at least one parameter of the water while the water is flowing across the surfaces of the plurality of electrodes.

* * * * *